United States Patent [19]

Hunkeler et al.

[11] Patent Number: 4,489,003
[45] Date of Patent: Dec. 18, 1984

[54] IMIDAZOBENZODIAZEPINES

[75] Inventors: Walter Hunkeler, Magden; Emilio Kyburz, Reinach, both of Switzerland

[73] Assignee: Hoffmann-La Roche Inc., Nutley, N.J.

[21] Appl. No.: 513,571

[22] Filed: Jul. 14, 1983

[30] Foreign Application Priority Data

Jul. 21, 1982 [CH] Switzerland ............ 4460/82

[51] Int. Cl.³ ............... C07D 471/14; C07D 471/22; C07D 513/22; A61K 31/55
[52] U.S. Cl. ............... 260/239.3 P; 260/239.3 T; 424/256; 424/273 R
[58] Field of Search ............... 260/239.3 T, 239.3 P

[56] References Cited

U.S. PATENT DOCUMENTS

| | | | |
|---|---|---|---|
| 4,316,839 | 2/1982 | Gerecke et al. | 260/239.3 P |
| 4,352,815 | 10/1982 | Hunkeler et al. | 260/239.3 P |
| 4,352,816 | 10/1982 | Hunkeler et al. | 260/239.3 P |
| 4,352,817 | 10/1982 | Hunkeler et al. | 260/239.3 P |
| 4,353,827 | 10/1982 | Hunkeler et al. | 260/239.3 P |

*Primary Examiner*—Robert T. Bond
*Attorney, Agent, or Firm*—Jon S. Saxe; Bernard S. Leon; Frank P. Hoffman

[57] ABSTRACT

There are described novel pharmaceutically active substances which have a pronounced affinity to the central benzodiazepine receptors and which have only a low toxicity.

These active substances, namely imidazobenzodiazepines of the formula

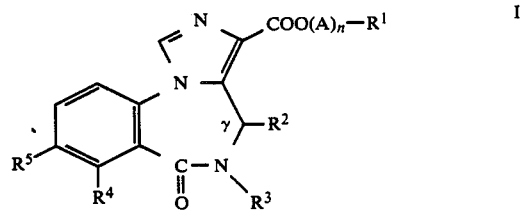

wherein A is lower alkylene, n is zero or 1, $R^1$ is lower alkynyl, lower alkenyl, aryl, ($C_{3-8}$)-cycloalkyl optionally substituted by lower alkyl or ($C_{5-8}$)-cycloalkenyl optionally substituted by lower alkyl, or a 5- or 6-membered saturated or unsaturated heterocycle which contains an oxygen or sulphur atom as a ring member and which is optionally substituted by lower alkyl, $R^4$ and $R^5$ each are hydrogen, halogen, trifluoromethyl, cyano, nitro, amino or lower alkyl and either $R^2$ is hydrogen and $R^3$ is lower alkyl or $R^2$ and $R^3$ together are dimethylene, trimethylene or propenylene, the compounds of formula I in which $R^2$ and $R^3$ together are dimethylene, trimethylene or propenylene having the (S) or (R,S) configuration with reference to the carbon atom denoted by $\gamma$, and their pharmaceutically acceptable acid addition salts, can be used as medicaments in the form of pharmaceutical preparations, especially in the control of convulsions and anxiety states and/or in the partial or complete antagonization of some or all activities which 1,4-benzodiazepines having tranquillizing activity or other substances display via the central benzodiazepine receptors.

22 Claims, No Drawings

IMIDAZOBENZODIAZEPINES

The present invention is concerned with imidazobenzodiazepines. In particular, it is concerned with tricyclic and tetracyclic imidazobenzodiazepines of the formula

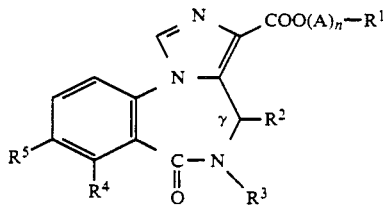

wherein A is lower alkylene, n is zero or 1, $R^1$ is lower alkynyl, lower alkenyl, aryl, $(C_{3-8})$-cycloalkyl optionally substituted by lower alkyl, $(C_{5-8})$-cycloalkenyl optionally substituted by lower alkyl, or a 5- or 6-membered saturated or unsaturated heterocycle which contains a oxygen or sulphur atom as a ring member and which is optionally substituted by lower alkyl, $R^4$ and $R^5$ each are hydrogen, halogen, trifluoromethyl, cyano, nitro, amino or lower alkyl and either $R^2$ is hydrogen and $R^3$ is lower alkyl or $R^2$ and $R^3$ together are dimethylene, trimethylene or propenylene, the compounds of formula I in which $R^2$ and $R^3$ together are dimethylene, trimethylene or propenylene having the (S) or (R,S) configuration with reference to the carbon atom denoted by γ, and pharmaceutically acceptable acid addition salts thereof.

These compounds are novel and are distinguished by valuable pharmacodynamic properties. They can be used in the control or prevention of illnesses.

The present invention relates to compounds of formula I and pharmaceutically acceptable acid addition salts thereof per se and as pharmaceutically active substances, the manufacture of these compounds, medicaments containing a compound of formula I or a pharmaceutically acceptable acid addition salt thereof, the manufacture of such medicaments and the use of the substances provided by the invention in the control or prevention of illnesses.

The term "lower" in combinations such as "lower alkyl", "lower alkyl groups", "lower alkylene", "lower alkyloxy", "lower alkynyl", "lower alkenyl" and the like signifies that the groups qualified thereby contain at most 7, preferably at most 4, carbon atoms. The terms "alkyl", "alkyl group" and the like denote straight-chain or branched-chain saturated hydrocarbon groups such as methyl, ethyl, n-propyl, isopropyl, n-butyl, s-butyl, t-butyl and the like. The term "alkyloxy" denotes alkyl groups linked via an oxygen atom such as, for example, methoxy, ethoxy, isopropoxy and the like. The term "alkylene" denotes divalent straight-chain or branched-chain saturated hydrocarbon groups such as methylene, 1,2-ethylene, ethylidene and the like. The term "alkynyl" denotes straight-chain or branched-chain hydrocarbon groups containing a triple bond such as propargyl and the like. The term "alkenyl" denotes straight-chain or branched-chain hydrocarbon groups containing a double bond such as allyl and the like.

The term "$(C_{3-8})$-cycloalkyl" denotes saturated cyclic hydrocarbon groups containing 3 to 8 ring members (i.e. cyclopropyl, cyclobutyl, cyclopentyl, cyclohexyl, cycloheptyl and cyclooctyl). The term "$(C_{5-8})$-cycloalkenyl" denotes unsaturated cyclic hydrocarbon groups containing 5 to 8 ring members such as 2-cyclohexen-1-yl and the like. The term "aryl" denotes phenyl or phenyl optionally substituted, preferably mono-substituted, by halogen, lower alkyloxy, lower alkyl, trifluoromethyl or nitro such as phenyl, o-chlorophenyl, m-chlorophenyl, p-chlorophenyl, o-methoxyphenyl, m-methoxyphenyl, p-methoxyphenyl and the like. The term "5- or 6-membered saturated or unsaturated heterocycle which contains oxygen or sulphur as a ring member" embraces heterocyclic groups containing one hetero atom such as tetrahydro-2H-pyran-4-yl and the like. The term "halogen" signifies fluorine, chlorine, bromine or iodine.

In a preferred embodiment, either n is zero or n is 1, whereby A is methylene or 1,2-ethylene optionally substituted by lower alkyl. $R^1$ preferably is alkynyl, phenyl, $(C_{3-8})$-cycloalkyl optionally substituted by lower alkyl or $(C_{5-8})$-cycloalkenyl optionally substituted by lower alkyl, with $(C_{3-6})$-cycloalkyl being especially preferred. In a particularly preferred embodiment, the group —$(A)_n$—$R^1$ is cyclohexyl, 2-cyclohexen-1-yl, cyclopropylmethyl, 1-cyclopropylethyl or 2-cyclopropylethyl.

Compounds of formula I in which $R^2$ and $R^3$ together are dimethylene, trimethylene or propenylene are preferred, these compounds preferably having the (S) configuration with respect to the carbon atom denoted by γ. $R^4$ preferably is hydrogen, halogen, trifluoromethyl, nitro, cyano or lower alkyl. $R^5$ preferably is hydrogen or halogen.

A particularly preferred compound provided by the present invention is:

Cyclopropylmethyl (S)-8-chloro-12,12a-dihydro-9-oxo-9H,11H-azeto[2,1-c]imidazo[1,5-a][1,4]benzodiazepine-1-carboxylate.

Other especially preferred compounds provided by the present invention are:

Cyclohexyl (S)-8-bromo-11,12,13,13a-tetrahydro-9-oxo-9H-imidazo[1,5-a]pyrrolo[2,1-c][1,4]benzodiazepine-1-carboxylate, (R,S)-2-cyclohexen-1-yl (S)-8-chloro-11,12,13,13a-tetrahydro-9-oxo-9H-imidazo[1,5-a]pyrrolo[2,1-c][1,4]benzodiazepine-1-carboxylate, cyclohexyl (S)-8-chloro-12,12a-dihydro-9-oxo-9H,11H-azeto[2,1-c]imidazo[1,5-a][1,4]benzodiazepine-1-carboxylate, cyclohexyl (S)-7-fluoro-12,12a-dihydro-9-oxo-9H,11H-azeto[2,1-c]imidazo[1,5-a][1,4]benzodiazepine-1-carboxylate, cyclohexyl (S)-8-chloro-7-fluoro-11,12,13,13a-tetrahydro-9-oxo-9H-imidazo[1,5-a]pyrrolo[2,1-c][1,4]benzodiazepine-1-carboxylate, (R,S)-1-cyclopropylethyl (S)-8-chloro-12,12a-dihydro-9-oxo-9H,11H-azeto[2,1-c]imidazo[1,5-a][1,4]benzodiazepine-1-carboxylate, cyclohexyl (S)-12,12a-dihydro-8-iodo-9-oxo-9H,11H-azeto[2,1-c]imidazo[1,5-a][1,4]benzodiazepine-1-carboxylate, cyclopropylmethyl (S)-7-fluoro-11,12,13,13a-tetrahydro-9-oxo-9H-imidazo[1,5-a]pyrrolo[2,1-c][1,4]benzodiazepine-1-carboxylate, (R,S)-1-cyclopropylethyl (S)-8-chloro-11,12,13,13a-tetrahydro-9-oxo-9H-imidazo[1,5-a]pyrrolo[2,1-c][1,4]benzodiazepine-1-carboxylate, cyclopropylmethyl (S)-7-fluoro-12,12a-dihydro-9-oxo-9H,11H-azeto[2,1-c]imidazo[1,5-a][1,4]benzodiazepine-1-carboxylate and cyclohexyl (S)-11,12,13,13a-tetrahydro-9-oxo-8-(trifluoromethyl)-9H-imidazo[1,5-a]pyrrolo[2,1-c][1,4]benzodiazepine-1-carboxylate.

Other preferred compounds of formula I are:

Cyclohexyl (S)-8-chloro-11,12,13,13a-tetrahydro-9-oxo-9H-imidazo[1,5-a]pyrrolo[2,1-c][1,4]benzodiazepine-1-carboxylate, 2-propynyl (S)-8-chloro-11,12,13,13a-tetrahydro-9-oxo-9H-imidazo[1,5-a]pyrrolo[2,1-c][1,4]benzodiazepine-1-carboxylate, cyclopropylmethyl 8-chloro-11,13a-dihydro-9-oxo-9H-imidazo[1,5-a]pyrrolo[2,1-c][1,4]benzodiazepine-1-carboxylate, cyclopropylmethyl (S)-8-chloro-11,12,13,13a-tetrahydro-9-oxo-9H-imidazo[1,5-a]pyrrolo[2,1-c][1,4]benzodiazepine-1-carboxylate, cyclopropylmethyl (S)-8-chloro-11,12,13,13a-tetrahydro-9-oxo-9H-imidazo[1,5-a]pyrrolo[2,1-c][1,4]benzodiazepine-1-carboxylate, cyclopropylmethyl (S)-11,12,13,13a-tetrahydro-8-iodo-9-oxo-9H-imidazo[1,5-a]pyrrolo[2,1-c][1,4]benzodiazepine-1-carboxylate, 2-cyclopropylethyl (S)-8-chloro-11,12,13,13a-tetrahydro-9-oxo-9H-imidazo[1,5-a]pyrrolo[2,1-c][1,4]benzodiazepine-1-carboxylate, cyclohexyl (S)-12,12a-dihydro-8-methyl-9-oxo-9H,11H-azeto[2,1-c]imidazo[1,5-a][1,4]benzodiazepine-1-carboxylate, rac-cis-3-methylcyclohexyl (S)-8-chloro-11,12,13,13a-tetrahydro-9-oxo-9H-imidazo[1,5-a]pyrrolo[2,1-c][1,4]benzodiazepine-1-carboxylate, cyclopentyl (S)-12,12a-dihydro-8-iodo-9-oxo-9H,11H-azeto[2,1-c]imidazo[1,5-a][1,4]benzodiazepine-1-carboxylate, cycloheptyl (S)-8-chloro-11,12,13,13a-tetrahydro-9-oxo-9H-imidazo[1,5-a]pyrrolo[2,1-c][1,4]benzodiazepine-1-carboxylate, benzyl (S)-8-chloro-12,12a-dihydro-9-oxo-9H,11H-azeto[2,1-c]imidazo[1,5-a][1,4]benzodiazepine-1-carboxylate, cyclopropylmethyl (S)-12,12a-dihydro-8-iodo-9-oxo-9H,11H-azeto[2,1-c]imidazo[1,5-a][1,4]benzodiazepine-1-carboxylate, cyclohexyl (S)-8-bromo-12,12a-dihydro-9-oxo-9H,11H-azeto[2,1-c]imidazo[1,5-a][1,4]benzodiazepine-1-carboxylate, cyclopropylmethyl (S)-8-bromo-12,12a-dihydro-9-oxo-9H,11H-azeto[2,1-c]imidazo[1,5-a][1,4]benzodiazepine-1-carboxylate, cyclohexyl (S)-11,12,13,13a-tetrahydro-8-nitro-9-oxo-9H-imidazo[1,5-a]pyrrolo[2,1-c][1,4]benzodiazepine-1-carboxylate and cyclohexyl (S)-8-cyano-11,12,13,13a-tetrahydro-9-oxo-9-imidazo[1,5-a]pyrrolo[2,1-c][1,4]benzodiazepine-1-carboxylate.

Examples of other compounds provided by the present invention are:

Cyclopropylmethyl (S)-11,12,13,13a-tetrahydro-9-oxo-8-(trifluoromethyl)-9H-imidazo[1,5-a]pyrrolo[2,1-c][1,4]-benzodiazepine-1-carboxylate, cyclohexyl (S)-12,12a-dihydro-9-oxo-8-(trifluoromethyl)-9H,11H-azeto[2,1-c]imidazo[1,5-a][1,4]benzodiazepine-1-carboxylate, cyclopropylmethyl (S)-12,12a-dihydro-9-oxo-8-(trifluoromethyl)-9H,11H-azeto[2,1-c]imidazo[1,5-a][1,4]-benzodiazepine-1-carboxylate, cyclopropylmethyl (S)-8-chloro-7-fluoro-11,12,13,13a-tetrahydro-9-oxo-9H-imidazo[1,5-a]pyrrolo[2,1-c][1,4]-benzodiazepine-1-carboxylate, cyclohexyl (S)-8-chloro-7-fluoro-12,12a-dihydro-9-oxo-9H-11H-azeto[2,1-c]imidazo[1,5-a][1,4]benzodiazepine-1-carboxylate, cyclopropylmethyl (S)-8-chloro-7-fluoro-12,12a-dihydro-9-oxo-9H,11H-azeto[2,1-c]imidazo[1,5-a][1,4]benzodiazepine-1-carboxylate, cyclohexyl (S)-8-fluoro-11,12,13,13a-tetrahydro-9-oxo-9H-imidazo[1,5-a]pyrrolo[2,1-c][1,4]benzodiazepine-1-carboxylate, cyclopropylmethyl (S)-8-fluoro-11,12,13,13a-tetrahydro-9-oxo-9H-imidazo[1,5-a]pyrrolo[2,1-c][1,4]benzodiazepine-1-carboxylate, cyclohexyl (S)-8-fluoro-12,12a-dihydro-9-oxo-9H,11H-azeto[2,1-c]imidazo[1,5-a][1,4]benzodiazepine-1-carboxylate and cyclopropylmethyl (S)-8-fluoro-12,12a-dihydro-9-oxo-9H,11H-azeto[2,1-c]imidazo[1,5-a][1,4]benzodiazepine-1-carboxylate.

The imidazobenzodiazepines of formula I above and their pharmaceutically acceptable acid addition salts can be manufactured in accordance with the invention by (a) trans-esterifying a carboxylic acid ester of the formula

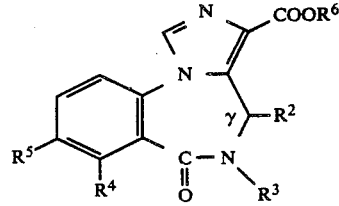

II wherein $R^6$ is lower alkyl or the group $—(A)_n—R^1$ and A, n, $R^1$, $R^2$, $R^3$, $R^4$ and $R^5$ are as above, with an alcohol of the formula $$HO—(A)_n—R^1 \qquad III$$

wherein A, n and $R^1$ are as above
which yields the desired group $—(A)_n—R^1$, or (b) esterifying a carboxylic acid of the formula

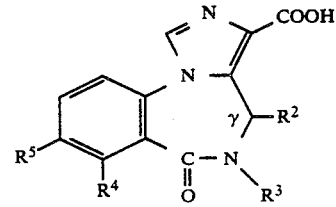

IV wherein $R^2$, $R^3$, $R^4$ and $R^5$ are as above,
with an agent which yields the group $—(A)_n—R^1$, or (c) reacting a compound of the formula

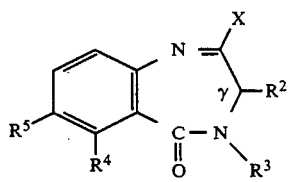

wherein X is a leaving group and $R^2$, $R^3$, $R^4$ and $R^5$ are as above, in the presence of a base with an isocyanoacetic ester of formula:

wherein A, n and $R^1$ are as above, or (d) replacing the halogen atom in a compound of formula I in which one of $R^4$ and R is halogen and the other is hydrogen, trifluoromethyl, amino, nitro, cyano or lower alkyl and A, n, $R^1$, $R^2$ and $R^3$ are as above by the cyano group, or (e) replacing the amino group in a compound of formula I in which one of $R^4$ and $R^5$ is amino and the other is hydrogen, halogen, trifluoromethyl, nitro, cyano or lower alkyl and A, n, $R^1$, $R^2$ and $R^3$ are as above by a hydrogen or halogen atom or by a cyano or nitro group, or (f) halogenating a compound of formula I in which one of $R^4$ and $R^5$ is amino and the other is hydrogen and A, n, $R^1$, $R^2$ and $R^3$ are as above in the α-position to the amino group, or (g) reducing the nitro group in a compound of formula I in which one of $R^4$ and $R^5$ is nitro and the other is hydrogen and A, n, $R^1$, $R^2$ and $R^3$ are as above to the amino group, and (h) if desired, converting a compound of formula I obtained into a pharmaceutically acceptable acid addition salt.

In accordance with process variant (a), the compounds of formula I can be manufactured by trans-esterifying compounds of formula II with an alcohol of formula III, i.e. by replacing the group $R^6$ in compounds of formula II by the desired group —$(A)_n$—$R^1$.

This trans-esterification is carried out in a manner known per se by reacting a compound of formula II with an alcohol of formula III in a temperature range of about room temperature to 150° C. The trans-esterification can be carried out, for example, in the presence of a base, potassium cyanide or similar weak bases being especially suitable in the present case. However, the sodium or potassium salt of an alcohol of formula III is also suitable as the base. The desired reaction can, however, also be carried out in the presence of a tetraalkyl orthotitanate such as tetraethyl orthotitanate, whereby tert.butyl esters can also be trans-esterified in the presence of such reagents. The alcohol of formula III is preferably used as the solvent In accordance with process variant (b), the compounds of formula I can be manufactured by esterifying a carboxylic acid of formula IV with an agent which yields the group —$(A)_n$—$R^1$. This esterification can be carried out according to methods which are known per se and which are familiar to any person skilled in the art. For example, a carboxylic acid of formula IV can be converted with a suitable reagent (e.g. with thionyl chloride, phosphorus oxychloride, oxalyl chloride or the like) into the corresponding carboxylic acid chloride and this can be reacted with an of formula III in the presence of an acid-binding agent. Tertiary amines such as triethylamine, pyridine, quinuclidine or the like are particularly suitable acid-binding agents. Under certain circumstances the presence of a catalytic amount of 4-dimethylaminopyridine or a similar reactive amine can be advantageous. This esterification can be carried out in two separate steps, i.e. formation of the reactive carboxylic acid derivative and reaction thereof with the alcohol of formula III, or in a so-called one-pot procedure which is preferred. Suitable solvents are, for example, halogenated hydrocarbons such as methylene chloride, chloroform, 1,2-dichloroethane and the like, ethers such as diethyl ether, tert.butyl methyl ether, tetrahydrofuran and the like, aprotic polar solvents such as acetonitrile, dimethylformamide etc. The esterification is conveniently carried out at temperature in the range of about −10° C. to the boiling point of the mixture.

It is, however, also possible to react a carboxylic acid chloride, obtained as described above, or a carboxylic acid imidazolide, which is readily accessible by reacting a free carboxylic acid of formula IV with N,N'-carbonyl-diimidazole, with a sodium or potassium salt of an alcohol of formula III. Ethers such as tetrahydrofuran and dioxan, aprotic polar solvents such as dimethylformamide and the like are especially suitable solvents. Depending on the solvent which is used the reaction is carried out in a temperature range of about 0° C. to about 100° C., but preferable at room temperature.

In accordance with process variant (c), the compounds of formula I can be manufactured from compounds of formula V and isocyanoacetic esters of formula VI. The leaving group denoted by X in formula V is, for example, a readily cleavable phosphinyl group, for example a group of the formula

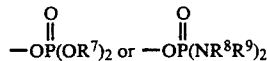

wherein $R^7$ is lower alkyl and $R^8$ and $R^9$ each are alkyl, allyl, phenyl or substituted phenyl or $R^8$ and $R^9$ together with the nitrogen atom are an unsubstituted or substituted heterocyclic ring containing 3-8 members (such as morpholine), a halogen atom, an alkylthio group, an aralkylthio group, a N-nitrosoalkylamino group, an alkoxy group, a mercapto group and the like (when X is a mercapto group, then the corresponding compound of formula V is the iminothiol form of the corresponding thiolactam). The reaction of a compound of formula V with a compound of formula VI is carried out in an inert solvent such as dimethylformamide, hexamethylphosphoric acid triamide, dimethyl sulphoxide tetrahydrofuran or any other suitable organic solvent and in the presence of a base which is sufficiently strongly basic to form the anion from the isocyanoacetic ester of formula VI. Alkali metal alkoxides such as sodium methoxide or potassium tert.butoxide, alkali metal hydrides such as sodium hydride, alkali metal amides such as lithium amide or lithium diisopropylamide, tertiary amines such as triethylamine and the like are suitable bases. The reaction is conveniently carried out at a temperature between about −40° C. and about room temperature.

In accordance with process variant (d), compounds of formula I in which one of $R^4$ and $R^5$ is cyano and the other is hydrogen, trifluoromethyl, amino, nitro, cyano or lower alkyl can be manufactured by replacing the halogen atom in a compound of formula I in which one of $R^4$ and $R^5$ is halogen and the other has the significance given earlier by the cyano group. A corresponding bromo or iodo compound is preferably used. The reaction can be carried out, for example, by reacting the corresponding bromo or iodo compound with copper (I) cyanide in an inert organic solvent. Suitable solvents are, for example, dimethylformamide and the like. The reaction is conveniently carried out in a temperature range of about room temperature to the boiling point of the reaction mixture.

In accordance with process variant (e), the amino group in a compound of formula I in which one of $R^4$ and $R^5$ is amino and the other is hydrogen, halogen, trifluoromethyl, nitro, cyano or lower alkyl is replaced by a hydrogen or halogen atom or by a cyano or nitro group. The replacement of the amino group by a halogen atom or by a cyano or nitro group can be carried out by converting the amino compound of formula I into a corresponding diazonium salt and reacting this, optionally without previous isolation, with a nitrite such as sodium nitrite or with a halide (e.g. a chloride or bromide) or with a cyanide in the presence of a copper (I) salt. The presence of a copper (I) salt is not necessary for the manufacture of the corresponding iodides. Corresponding fluorides are conveniently manufactured via the corresponding diazonium-tetrafluoroborates, for example by irradiation with UV light. These reactions are carried out in aqueous solutions at temperatures from about $-10°$ C. to about room temperature.

The replacement of an amino group in a compound of formula I by the nitro group can, however, also be carried out by oxidizing an amino compound of formula I. Suitable oxidizing agents are, for example, peracids such as peracetic acid, trifluoroperacetic acid, m-chloroperbenzoic acid and perbenzoic acid and the like. As solvents there come into consideration, depending on the oxidizing agent which is used, carboxylic acids such as acetic acid etc, halogenated hydrocarbons such as methylene chloride, chloroform, 1,2-dichloroethane etc, or the like. This oxidation is generally carried out at temperatures from about 0° C. to about room temperature.

The replacement of the amino group by a hydrogen atom can be carried out, for example, by reducing a corresponding diazonium salt, for example by heating in a cyclic ether such as tetrahydrofuran or dioxan or in dimethylformamide; the heating being preferably carried out at the boiling point of the mixture. However, in an especially preferred embodiment an amine of formula I is reacted with t-butyl nitrite in a cyclic ether such as tetrahydrofuran or dioxan, the reaction being preferably carried out at the boiling point of the mixture.

In accordance with process variant (f), a compound of formula I in which one of $R^4$ and $R^5$ is amino and the other is hydrogen can be halogenated in the α-position to the amino group. Suitable halogenating agents are, for example, N-chlorosuccinimide, N-bromo-succinimide, N-chloroacetamide, N-bromoacetamide and the like. As solvents there are conveniently used inert organic solvents, for example halogenated hydrocarbons such as methylene chloride, 1,2-dichloroethane, chloroform and the like, dimethylformamide, dimethylacetamide, acetonitrile, ethers such as diethyl ether, tetrahydrofuran, dioxan and the like, etc. The halogenation can be carried out at a temperature in the range of about 0° C. to the boiling point of the mixture, a range of about room temperature to about 100° C. being preferred.

In accordance with process variant (g), compounds of formula I in which one of $R^4$ and $R^5$ is amino and the other is hydrogen can be manufactured by reducing a corresponding nitro compound. There are conveniently used reducing agents such as tin (II) chloride, tin, zinc and the like in an acidic-aqueous medium, for example in aqueous hydrochloric acid, concentrated hydrochloric acid or the like, at a temperature in the range of about 0° C. to about room temperature.

In accordance with process variant (h), compounds of formula I can be converted into pharmaceutically acceptable acid addition salts. The manufacture of such pharmaceutically acceptable acid addition salts is carried out according to generally customary methods. There come into consideration not only salts with inorganic acids but also salts with organic acids; for example, hydrochlorides, hydrobromides, sulphates, methanesulphonates, p-toluene-sulphonates, oxalates and the like.

The compounds of formula II in which $R^6$ is lower alkyl which are used as starting materials are known compounds or can be prepared in analogy to the known members of this class of substance. For example, they can be prepared readily in analogy to process variant (c) described above by reacting a compound of formula V with an isocyanoacetic ester of the formula

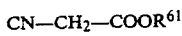

$$CN-CH_2-COOR^{61} \qquad VII$$

wherein $R^{61}$ is lower alkyl,
in the presence of a base.

The compounds of formula IV which are used as starting materials are readily accessible by hydrolyzing the ester group in compounds of formula II in which $R^6$ is lower alkyl according to methods which are known per se and which are familiar to any person skilled in the art. These compounds also belong to a class of substance which is known per se.

The starting materials of formula V also belong to a class of substance which is known per se and can be prepared starting from compounds of the formula

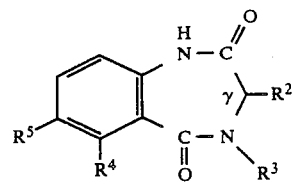

wherein $R^2$, $R^3$, $R^4$ and $R^5$ are as above,
according to methods known per se; see, for example, Belgian patent specifications Nos. 802 233, 833 249 and 865 653, U.S. Pat. No. 3,681,341 and J. Org. Chemistry 29, 231 (1964).

Certain Examples hereinafter contain detailed information concerning the preparation of compounds of formulae II, IV and V.

The compounds of formula VIII are also known or can be prepared readily according to methods known per se. For example, they can be prepared by reacting a corresponding carboxylic acid anhydride of the formula

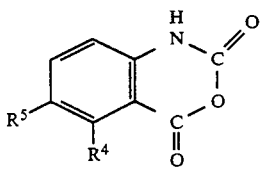

wherein R⁴ and R⁵ are as above,
with an amino acid of the formula

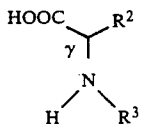

wherein R² and R³ are as above.

Compounds of formula VIII in which one of R⁴ and R⁵ is halogen and the other is hydrogen, trifluoromethyl, amino, nitro, cyano or lower alkyl can be converted into corresponding cyano compounds by treatment with copper (I) cyanide. Furthermore, the amino group in a compound of formula VIII in which one of R⁴ and R⁵ is amino and the other is hydrogen, halogen, trifluoromethyl, nitro, cyano or lower alkyl can be cleaved off, for example by reducing a corresponding diazonium salt, or can be replaced by a halogen atom or by the cyano or nitro group via a corresponding diazonium salt or can be oxidized to the nitro group. Finally, a compound of formula VIII in which R⁴ and R⁵ are hydrogen can be nitrated, there being obtained a corresponding compound of formula VIII in which R⁵ is nitro and R⁴ is hydrogen, or a compound of formula VIII in which one of R⁴ and R⁵ is nitro can be reduced to the corresponding amino compound.

As mentioned earlier, the compounds of formula I are novel; they possess extremely valuable pharmacodynamic properties and have only a low toxicity. They possess as a common characteristic a pronounced affinity to the central benzodiazepine receptors and have either pronounced anxiolytic, anticonvulsant, muscle relaxant and sedative-hypnotic properties and/or they selectively antagonise partially or completely some or all of the activities which are displayed by 1,4-benzodiazpines having tranquillizing activity or other substances via the central benzodiazepine receptors.

The affinity of compounds of general formula I to the central benzodiazepine receptors was determined according to the method described in Life Science 20, 2101–2110 (1977) and Science 198, 849–851 (1977). According to this method, the inhibition of the binding of tritiated diazepam at the specific benzodiazepine receptors in the cerebral cortex by the respective test substances is ascertained. The IC$_{50}$ ("50% inhibiting concentration") is that concentration of the respective test substance which brings about a 50 percent inhibition of the specific binding of the tritiated diazepam at the specific benzodiazepine receptors in the cerebral cortex.

The central properties of the compounds of formula I provided by the present invention can be determined, for example, in the antipentetrazole test which is described hereinafter and which is generally recognized for recording anticonvulsant properties.

In this animal experiment the compound under investigation is administered orally to female rats weighing 60–80 g and 30 minutes later there are administered intraperitoneally 120 mg/kg of pentetrazole which causes emprosthotonus and tonic stretchings of the fore and/or hind limbs in unprotected experimental animals 1 to 4 minutes after the injection. Ten experimental animals are used per dosage of test substance. After counting the protected experimental animals, the ED$_{50}$ is determined according to the Probit method. The ED$_{50}$ is that dosage which protects 50% of the experimental animals from the spasmodic seizures caused by pentetrazole.

The antagonistic properties of the compounds of formula I, i.e. their ability to antagonise activities which 1,4-benzodiazepines having tranquillizing activity or other substances display via the central benzodiazepine receptors, can be demonstrated, for example, in the known traction test described hereinafter. In this animal experiment the ability of the test substances to antagonise the sedative, muscle relaxant and motor coordination-disturbing activity caused by high dosages of diazepam is determined.

Mice weighing 17–29 g are lifted by the tail and are allowed to grip a taut horizontal wire (length 15 cm, height 20 cm, diameter 1 mm) with the front paws, whereupon the experimental animals are released. Untreated control animals are capable of gripping the wire with both front paws and at least one hind paw within 3 seconds. If 3 mg/kg of diazepam are administered intraperitoneally to the experimental animals, then their aforementioned capabilities disappear, i.e. they are no longer capable of gripping the taut horizontal wire within 3 seconds with both front paws and at least one hind paw. 15 minutes after the administration of diazepam the compound under investigation is administered orally to the experimental animals, whereupon there are counted those animals which have regained the aforementioned capabilities. The ED$_{50}$ is that dosage which in 50% of the experimental animals antagonizes the action of diazepam, i.e. counteracts this.

The results obtained with representative compounds of formula I in the experiments described earlier are compiled in the following Table. The Table also contains data concerning the acute toxcity of some of these compounds (LD$_{50}$ in mg/kg following single oral administration to rats).

TABLE

| Compound of formula I in which | | | | | Configuration | IC$_{50}$ in μM/l | Antipentetrazole test, ED$_{50}$ in mg/kg p.o. | Traction test, ED$_{50}$ in mg/kg p.o. | Toxicity, LD$_{50}$ in mg/kg p.o. |
|---|---|---|---|---|---|---|---|---|---|
| —(A)$_n$—R¹ | R² | R³ | R⁴ | R⁵ | | | | | |
|  —CH$_2$—◁ | —CH$_2$—CH$_2$—CH$_2$— | | Cl | H | (S) | 2.3 | 0.66 | 0.8 | 1000–2000 |
|  —CH$_2$—◁ | —CH$_2$—CH$_2$— | | Cl | H | (S) | 1.1 | 0.27 | <30 | — |
|  —◁ | —CH$_2$—CH$_2$—CH$_2$— | | Cl | H | (S) | 2.2 | 2.9 | 0.5 | — |

TABLE-continued

| Compound of formula I in which −(A)$_n$−R$^1$ | R$^2$ | R$^3$ | R$^4$ | R$^5$ | Configuration | IC$_{50}$ in μM/l | Antipentetrazole test, ED$_{50}$ in mg/kg p.o. | Traction test, ED$_{50}$ in mg/kg p.o. | Toxicity, LD$_{50}$ in mg/kg p.o. |
|---|---|---|---|---|---|---|---|---|---|
| −CH$_2$−phenyl | | −CH$_2$−CH$_2$−CH$_2$− | Cl | H | (S) | 1.5 | >100 | 0.09 | − |
| −CH$_2$−C≡CH | | −CH$_2$−CH$_2$−CH$_2$− | Cl | H | (S) | 2.1 | >100 | 0.005 | − |
| −cyclohexyl | | −CH$_2$−CH$_2$−CH$_2$− | Br | H | (S) | 2.7 | 7.0 | <30 | >5000 |
| −CH$_2$−cyclopropyl | | −CH$_2$−CH$_2$−CH$_2$− | Br | H | (S) | 2.6 | 0.63 | <30 | 625−1250 |
| −cyclohexyl | | −CH$_2$−CH$_2$−CH$_2$− | I | H | (S) | 2.1 | 2.2 | >30 | >5000 |

A selective antagonistic component, as can be demonstrated in the case of many of the compounds of formula I, is of great therapeutic significance, in that it permits the use of desired properties (e.g. anxiolytic or anticonvulsant activity) of the substances in accordance with the invention while suppressing additional properties (e.g. sedative, muscle relaxant and motor coordination-disturbing activities) which are undesired in certain fields of application.

The compounds of formula I and their pharmaceutically acceptable acid addition salts can be used as medicaments, for example in the form of pharmaceutical preparations. The pharmaceutical preparations can be administered orally, for example in the form of tablets, coated tablets, dragées, hard and soft gelatine capsules, solutions, emulsions or suspensions. The administration can, however, also be carried out rectally (e.g. in the form of suppositories) or parenterally (e.g. in the form of injection solutions).

For the manufacture of pharmaceutical preparations the products provided by the present invention can be processed with pharmaceutically inert, inorganic or organic carriers. Examples of such carriers which can be used for tablets, coated tablets, dragées and hard gelatine capsules are lactose, maize starch or derivatives thereof, talc, stearic acid or its salts etc. Suitable carriers for soft gelatine capsules are, for example, vegetable oils, waxes, fats, semi-solid and liquid polyols and the like; depending on the nature of the active substance no carriers are, however, generally required in the case of soft gelatine capsules. Suitable carriers for the manufacture of solutions and syrups are, for example, water, polyols, saccharose, invert sugar, glucose and the like. Suitable carriers for injection solutions are, for example, water, alcohols, polyols, glycerine, vegetable oils and the like. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, colouring agents, flavouring agents, salts for varying the osmotic pressure, buffers, coating agents or antioxidants. They can also contain still other therapeutically valuable substances.

As mentioned earlier, medicaments containing a compound of formula I or a pharmaceutically acceptable acid addition salt thereof are also an object of the present invention as is a process for the manufacture of such medicaments, which process comprises bringing one or more compounds of formula I or pharmaceutically acceptable acid addition salts thereof and, if desired, one or more other therapeutically valuable substances into a galenical administration form.

As mentioned earlier, the compounds of formula I and their pharmaceutically acceptable acid addition salts can be used in the control or prevention of illnesses, especially in the control of convulsions and anxiety states and/or in the partial or complete antagonisation of some or all activities which 1,4-benzodiazepines having tranquillizing activity or other substances display via the central benzodiazepine receptors. The dosage can vary within wide limits and is, of course, fitted to the individual requirements in each particular case. In general, a daily dosage of about 0.1 mg to 100 mg should be appropriate.

The following Examples illustrate the present invention in more detail, but are not intended to limit its extent. In the Examples all temperatures are given in degrees Centigrade.

EXAMPLE 1

A mixture of 10.37 g (0.03 mol) of ethyl (S)-8-chloro-11,12,13,13a-tetrahydro-9-oxo-9H-imidazo[1,5-a]pyrrolo[2,1-c][1,4]benzodiazepine-1-carboxylate, 35 ml of hydroxymethyl-cyclopropane and 0.5 g of potassium cyanide is stirred at 125° for 12 hours, during this time three 2–3 ml portions of the solvent being distilled off by the application of a slight vacuum. The mixture is subsequently evaporated in vacuo, the residue is partitioned between chloroform and water, the chloroform solution is washed successively with water and saturated sodium chloride solution, dried over magnesium sulphate and evaporated. The residue obtained is recrystallized from ethyl acetate, there being obtained cyclopropylmethyl (S)-8-chloro-11,12,13,13a-tetrahydro-9-oxo-9H-imidazo[1,5-a]pyrrolo[2,1-c][1,4]benzodiazepine-1-carboxylate of melting point 195°–196°.

EXAMPLE 2

(a) 11.3 g (0.057 mol) of 6-chloroisatoic acid anhydride and 5.78 g (0.057 mol) of L-azetidinecarboxylic acid are heated to 125° for 2 hours in 50 ml of dimethyl sulphoxide. The mixture is subsequently evaporated to dryness in a high vacuum and the residue obtained is heated to 150° for 2 hours. By chromatography on silica gel while eluting with ethyl acetate there is obtained (S)-5-chloro-1,10a-dihydroazeto[2,1-c][1,4]benzodiaze-pine4,10(2H,9H)-dione of melting point 225°-228°.

(b) A suspension of 1.30 g (29.8 mmol) of sodium hydride (55 percent oil dispersion) in 40 ml of dry dimethylformamide is treated at −15° with 6.38 g (27 mmol) of (S)-5-chloro-1,10a-dihydroazeto[2,1-c][1,4]benzodiazepine-4,10(2H,9H)-dione and the mixture is stirred at this temperature for 0.5 hour. The mixture is subsequently cooled to −35° and treated dropwise with 4.8 ml (29.8 mmol) of diethylchlorophosphate.

Separately, a solution of 3.55 g (32.4 mmol) of potassium tert.butylate in 14 ml of dry dimethylformamide is cooled in an acetone/dry-ice bath, treated with 4.1 ml (32.4 mmol) of ethyl isocyanoacetate and the mixture obtained is added dropwise at −10° to the mixture obtained according to the preceding paragraph. The cooling bath is removed, the mixture is stirred for about a further 15 minutes, neutralized with glacial acetic acid, poured into 100 ml of water and extracted three times with chloroform. The combined chloroform extracts are washed three times with water, dried over magnesium sulphate and evaporated. The crude product obtained is chromatographed on silica gel and subsequently recrystallized from ethyl acetate. There is obtained ethyl (S)-8-chloro-12,12a-dihydro-9-oxo-9H,11H-azeto[2,1-c]imidazo[1,5-a][1,4]benzodiazepine-1-carboxylate of melting point 184°-185°.

(c) A mixture of 8.0 g (24 mmol) of ethyl (S)-8-chloro-12,12a-dihydro-9-oxo-9H,11H-azeto[2,1-c]imidazo[1,5-a][1,4]benzodiazepine-1-carboxylate, 0.5 g (7.7 mmol) of potassium cyanide and 60 ml of hydroxymethyl-cyclopropane is stirred at 130° for 5 hours, during this time a small amount of solvent being distilled off four times by the application of a slight vacuum. The mixture is subsequently evaporated in vacuo, the residue is partitioned between water and methylene chloride and the aqueous phase is extracted twice with methylene chloride. The combined organic extracts are washed three times with saturated sodium chloride solution, dried over magnesium sulphate and evaporated. The crude product is crystallized from ethyl acetate and there is obtained cyclopropylmethyl (S)-8-chloro-12,12a-dihydro-9-oxo-9H,11H-azeto[2,1-c]imidazo[1,5-a][1,4]benzodiazepine-1-carboxylate of decomposition point 183°-185° (partially racemized).

By chromatography of the mother liquor on silica gel while eluting with ethyl acetate there is obtained a second portion of the desired substance having the same purity.

EXAMPLE 3

(a) 9.2 g (0.038 mol) of 6-bromo-isatoic acid anhydride and 4.6 g (0.040 mol) of L-proline in 55 ml of dimethyl sulphoxide are heated to 70° for 1 hour, the solvent is removed in a high vacuum and the oil obtained is heated to 170° for 15 minutes. The crude product is purified by chromatography on silica gel using a mixture of chloroform and methanol (20:1) for the elution. There is obtained (S)-6-bromo-1,2,3,11a-tetrahydro-5H-pyrrolo[2,1-c][1,4]benzodiazepine-5,11(10H)-dione which melts at 221°-224° after recrystallization from chloroform/hexane.

(b) A solution of 9.94 g (33.7 mmol) of (S)-6-bromo-1,2,3,11a-tetrahydro-5H-pyrrolo[2,1-c][1,4]benzodiazepine-5,11(10H)-dione in 30 ml of dry dimethylformamide is treated at −20° to −10° while stirring with 1.62 g (37 mmol) of sodium hydride (55 percent oil dispersion), the mixture is stirred in the above temperature range for a further 1.25 hours and then 5.5 ml (37 mmol) of diethylchlorophosphate are added dropwise thereto at −40°.

Separately, 4.15 g (37 mmol) of potassium tert.butylate are dissolved in 10 ml of dry dimethylformamide, the solution is cooled in an acetone/dry-ice bath, treated with 5.22 g (37 mmol) of tert.butyl isocyanoacetate and the solution obtained is added dropwise at −15° to the mixture obtained according to the preceding paragraph. The resulting mixture is allowed to warm to 10°, neutralized with 2.1 ml of glacial acetic acid, poured into 150 ml of water and extracted three times with methylene chloride. The methylene chloride solution is washed twice with water, dried over magnesium sulphate and evaporated. The crude product obtained is chromatographed on silica gel while eluting with ethyl acetate. By recrystallization from ethyl acetate there is obtained tert.butyl (S)-8-bromo-11,12,13,13a-tetrahydro-9-oxo-9H-imidazo[1,5-a]pyrrolo[2,1-c][1,4]benzodiazepine-1-carboxylate of melting point 206°-208°.

(c) A mixture of 10 g (24 mmol) of tert.butyl (S)-8-bromo-11,12,13,13a-tetrahydro-9-oxo-9H-imidazo[1,5-a]pyrrolo[2,1-c][1,4]benzodiazepine-1-carboxylate, 30 g (300 mmol) of cyclohexanol and 1.80 g (8 mmol) of tetraethyl orthotitanate is stirred at 125° overnight, the solution obtained is evaporated to dryness, the residue is taken up in chloroform and stirred for 0.5 hour with 40 ml of a saturated potassium fluoride solution. The resulting emulsion is filtered through siliceous earth, the organic phase is separated, washed with water, dried over magnesium sulphate and evaporated. By recrystallization of the residue from ethyl acetate there is obtained cyclohexyl (S)-8-bromo-11,12,13,13a-tetrahydro-9-oxo-9H-imidazo[1,5-a]-pyrrolo[2,1-c][1,4]benzodiazepine-1-carboxylate of melting point 167°-168°.

EXAMPLE 4

(a) A suspension of 91 g (308 mmol) of (S)-6-bromo-1,2,3,11a-tetrahydro-5H-pyrrolo[2,1-c][1,4]benzodiazepine-5,11-(10H)-dione in 300 ml of dry dimethylformamide is treated while stirring at 0° with 38 g (339 mmol) of potassium tert.butylate, the mixture is stirred at 10°-20° for 0.5 hour and subsequently 58 g (339 mmol) of diethylchlorophosphate are added dropwise thereto at −20°.

Separately, 38 g (339 mmol) of potassium tert.butylate are dissolved in 100 ml of dry dimethylformamide, the solution is cooled in an acetone/dry-ice bath, treated with 38.34 g (339 mmol) of ethyl isocyanoacetate and the thus-obtained solution is added dropwise at −15° to the mixture obtained according to the preceding paragraph. The resulting mixture is allowed to warm to room temperature, poured into 1500 ml of water and stirred for 1 hour. The mixture is subsequently extracted three times with methylene chloride, the organic phase is washed twice with water, dried over magnesium sulphate and the solvent is removed by distillation. The crude product is chromatographed on silica gel while eluting with ethyl acetate and then recrystallized from ethyl acetate. There is obtained ethyl (S)-8-bromo-11,12,13,13a-tetrahydro-9-oxo-9H-imidazo[1,5-a]pyrrolo[2,1-c][1,4]benzodiazepine-1-carboxylate of melting point 191°–192°.

(b) A mixture of 9.50 g (24.3 mmol) of ethyl (S)-8-bromo-11,12,13,13a-tetrahydro-9-oxo-9H-imidazo[1,5-a]pyrrolo[2,1-c][1,4]benzodiazepine-1-carboxylate, 60 ml (560 mmol) of cyclohexanol and 300 mg of powdered potassium cyanide is stirred at 130° for 24 hours, a small amount of cyclohexanol being distilled off from time to time. The solution obtained is subsequently evaporated to dryness, the residue is taken up in chloroform, washed with water and dried over magnesium sulphate. After removal of the solvent, the residue is chromatographed on a silica gel column while eluting with ethyl acetate and subsequently recrystallized from ethyl acetate. There is obtained cyclohexyl (S)-8-bromo-11,12,13,13a-tetrahydro-9-oxo-9H-imidazo[1,5-a]pyrrolo[2,1-c][1,4]benzodiazepine-1-carboxylate of melting point 167°–168°.

EXAMPLE 5

A mixture of 12 g (31 mmol) of ethyl (S)-8-bromo-11,12,13,13a-tetrahydro-9-oxo-9H-imidazo[1,5-a]pyrrolo[2,1-c][1,4]benzodiazepine-1-carboxylate, 60 ml (750 mmol) of hydroxymethyl-cyclopropane and 500 mg of powdered potassium cyanide is stirred at 135° for 1.5 hours, the alcohol being simultaneously distilled off over a Hickmann headpiece and a 15 cm Vigreux column. The mixture is evaporated to dryness, the residue is taken up in chloroform, washed with water, dried over magnesium sulphate and evaporated. By recrystallization from ethyl acetate there is obtained cyclopropylmethyl (S)-8-bromo-11,12,13,13a-tetrahydro-9-oxo-9H-imidazo[1,5-a]pyrrolo[2,1-c][1,4]benzodiazepine-1-carboxylate of melting point 135°–136°.

EXAMPLE 6

A mixture of 10 g (24 mmol) of tert.butyl (S)-8-bromo-11,12,13,13a-tetrahydro-9-oxo-9H-imidazo[1,5-a]pyrrolo[2,1-c][1,4]benzodiazepine-1-carboxylate, 31 g (430 mmol) of hydroxymethyl-cyclopropane and 1.80 g (8 mmol) of tetraethyl orthotitanate is stirred at 125° overnight, the solution obtained is evaporated to dryness, the residue is taken up in chloroform and stirred for 0.5 hour with 40 ml of a saturated potassium fluoride solution. The resulting emulsion is filtered through siliceous earth, the organic phase is separated, washed with water, dried over magnesium sulphate and evaporated. By recrystallization from ethyl acetate and hexane there is obtained cyclopropylmethyl (S)-8-bromo-11,12,13,13a-tetrahydro-9-oxo-9H-imidazo[1,5-a]pyrrolo[2,1-c][1,4]benzodiazepine-1-carboxylate of melting point 135°–136°.

EXAMPLE 7

(a) 70 g (242 mmol) of 6-iodoisatoic acid anhydride and 24.46 g (242 mmol) of L-azetidine-2-carboxylic acid in 140 ml of dimethyl sulphoxide are stirred at 105° for 2 hours, the dimethyl sulphoxide is removed in vacuo and the residue is heated to 140° in a high vacuum for 2.5 hours. By chromatography on silica gel while eluting with ethyl acetate and subsequent recrystallization from ethyl acetate there is obtained (S)-1,10a-dihydro-5-iodo-azeto[2,1-c][1,4]benzodiazepine-4,10(2H,9H)-dione of melting point 186°–187°.

(b) 23.6 g (72 mmol) of (S)-1,10a-dihydro-5-iodo-azeto[2,1-c][1,4]benzodiazepine-4,10(2H,9H)-dione in 70 ml of dry dimethylformamide are treated with 2.04 g (85 mmol) of sodium hydride (55 percent oil dispersion, washed with n-hexane), the mixture is stirred at −20° for 1 hour, then treated dropwise at this temperature with 13.8 g of diethylchlorophosphate and the mixture is stirred at −20° for a further 0.5 hour.

Separately, 9.53 g (85 mmol) of potassium tert.butylate are dissolved in 20 ml of dry dimethylformamide, the solution is cooled in an acetone/dry-ice bath, treated with 11.9 g (85 mmol) of tert.butyl isocyanoacetate and the thus-obtained solution is added dropwise at −10° to −20° to the mixture obtained according to the preceding paragraph. The mixture is allowed to warm to room temperature, poured into about 700 ml of water and stirred for 1 hour. The mixture is then extracted three times with methylene chloride, washed twice with water, dried over magnesium sulphate and the solvent is removed by distillation. By chromatography on silica gel while eluting with ethyl acetate and subsequent recrystallization from ethyl acetate there is obtained tert.butyl (S)-12,12a-dihydro-8-iodo-9-oxo-9H,11H-azeto[2,1-c]imidazo[1,5-a][1,4]benzodiazepine-1-carboxylate of melting point 249°–250°.

(c) 3.0 g (5.5 mmol) of tert.butyl (S)-12,12a-dihydro-8-iodo-9-oxo-9H,11H-azeto[2,1-c]imidazo[1,5-a][1,4]benzodiazepine-1-carboxylate, 20 ml (250 mmol) of hydroxymethyl-cyclopropane and 0.7 g (3 mmol) of tetraethyl orthotitanate are stirred at 120° overnight, the solution is evaporated to dryness, the residue is taken up in chloroform and stirred for 0.5 hour with 30 ml of a saturated potassium fluoride solution. The resulting emulsion is filtered through siliceous earth, the organic phase is separated, washed with water, dried over magnesium sulphate and evaporated. By recrystallization from ethyl acetate there is obtained cyclopropylmethyl (S)-12,12a-dihydro-8-iodo-9-oxo-9H,11H-azeto[2,1-c]imidazo[1,5-a][1,4]benzodiazepine-1-carboxylate of melting point 190°–191°.

EXAMPLE 8

(a) 14.6 g (0.050 mol) of 6-iodo-isatoic acid anhydride and 6.6 g (0.058 mol) of L-proline in 50 ml of dimethyl sulphoxide are heated to 70° for 30 minutes, the solvent is removed in a high vacuum and the oil obtained is heated to 170° for 15 minutes. The crude product is purified by chromatography on silica gel using methylene chloride and a mixture of methylene chloride and ethyl acetate for the elution. There is obtained (S)-1,2,3,11a-tetrahydro-6-iodo-5H-pyrrolo[2,1-c][1,4]benzodiazepine-5,11(10H)-dione which melts at 212°–215° after recrystallization from methanol.

(b) A solution of 10.0 g (29.2 mmol) of (S)-1,2,3,11a-tetrahydro-6-iodo-5H-pyrrolo[2,1-c][1,4]benzodiazepine-5,11(10H)-dione in 30 ml of dry dimethylformamide is treated at −20° while stirring with 1.4 g (32.1 mmol) of sodium hydride (55 percent oil dispersion), the mixture is stirred at the above temperature for a further 1 hour and subsequently 4.8 ml (32.1 mmol) of diethylchlorophosphate are added dropwise thereto at −45°.

Separately, 3.6 g (32.1 mmol) of potassium tert.butylate are dissolved in 8 ml of dry dimethylformamide, the solution is cooled in an acetone/dry-ice bath, treated with 4.5 g (32.1 mmol) of tert.butyl isocyanoacetate and the solution obtained is added dropwise at −20° to the mixture obtained according to the preceding paragraph. The resulting mixture is stirred at −20° for a further 15 minutes, neutralized with 1.9 ml of glacial acetic acid, poured into 150 ml of water and extracted three times with methylene chloride. The organic extracts are washed twice with water, dried over magnesium sulphate and evaporated. The crude product obtained is chromatographed on silica gel while eluting with ethyl acetate containing 30% n-hexane and subsequently recrystallized from ethyl acetate. There is obtained tert.butyl (S)-11,12,13,13a-tetrahydro-8-iodo-9-oxo-9H-imidazo[1,5-a]pyrrolo[2,1-c][1,4]benzodiazepine-1-carboxylate of melting point 241°–242°.

(c) 5 g (11 mmol) of tert.butyl (S)-11,12,13,13a-tetrahydro-8-iodo-9-oxo-9H-imidazo[1,5-a]pyrrolo[2,1-c][1,4]benzodiazepine-1-carboxylate, 30 g (300 mmol) of cyclohexanol and 1 g (4 mmol) of tetraethyl orthotitanate are stirred at 125° overnight, the solution is evaporated to dryness and the residue is taken up in chloroform. The solution is then stirred for 0.5 hour with 40 ml of a saturated potassium fluoride solution, the resulting emulsion is filtered over siliceous earth, the organic phase is separated, washed with water, dried over magnesium sulphate and evaporated. By crystallization from ethyl acetate there is obtained cyclohexyl (S)-11,12,13,13a-tetrahydro-8-iodo-9-oxo-9H-imidazo[1,5-a]pyrrolo[2,1-c][1,4]benzodiazepine-1-carboxylate of melting point 181°–182°.

EXAMPLE 9

12 g (26.6 mmol) of tert.butyl (S)-12,12a-dihydro-8-iodo-9-oxo-9H,11H-azeto[2,1-c]imidazo[1,5-a][1,4]benzodiazepine-1-carboxylate, 70 ml (660 mmol) of cyclohexanol and 2 g (8 mmol) of tetraethyl orthotitanate are stirred at 120° overnight, the solution is evaporated to dryness and the residue is taken up in chloroform. The solution obtained is stirred for 0.5 hour with 120 ml of a saturated potassium fluoride solution, the resulting emulsion is filtered through siliceous earth, the organic phase is separated, washed with water, dried over magnesium sulphate and evaporated. By crystallization from ethyl acetate and hexane there is obtained cyclohexyl (S)-12,12a-dihydro-8-iodo-9-oxo-9H,11H-azeto[2,1-c]imidazo[1,5-a][1,4]benzodiazepine-1-carboxylate of melting point 124°–125°.

EXAMPLE 10

4.65 g (10 mmol) of tert.butyl (S)-11,12,13,13a-tetrahydro-8-iodo-9-oxo-9H-imidazo[1,5-a]pyrrolo[2,1-c][1,4]benzodiazepine-1-carboxylate, 24 g (330 mmol) of hydroxymethyl-cyclopropane and 3 g (13 mmol) of tetraethyl crthotitanate are stirred at 115° overnight, the solution is evaporated to dryness and the residue is taken up in chloroform. The solution obtained is stirred for 0.5 hour with 40 ml of a saturated potassium fluoride solution, the resulting emulsion is filtered through siliceous earth, the organic phase is separated, washed with water, dried over magnesium sulphate and evaporated. By crystallization from ethyl acetate and hexane there is obtained cyclopropylmethyl (S)-11,12,13,13a-tetrahydro-8-iodo-9-oxo-9H-imidazo[1,5-a]pyrrolo[2,1-c][1,4]benzodiazepine-1-carboxylate of melting point 164°–165°.

EXAMPLE 11

(a) A mixture of 4.8 g (24.3 mmol) of 6-chloro-isatoic acid anhydride, 2.83 g (25 mmol) of (L)-3,4-dehydroproline and 20 ml of dimethyl sulphoxide is stirred at 100° for 1.25 hours, subsequently poured into 200 ml of water and extracted three times with ethyl acetate. The ethyl acetate solution is washed once with water, dried over magnesium sulphate, filtered and evaporated. The residue obtained is chromatographed on silica gel and subsequently crystallized from ethyl acetate, there being obtained (S)-6-chloro-3,11a-dihydro-5H-pyrrolo[2,1-c][1,4]benzodiazepine-5,11(10H)-dione of melting point 254°–256°.

(b) A suspension of 1.9 g (44.6 mmol) of sodium hydride (55 percent oil dispersion) in 80 ml of dry dimethylformamide is treated while stirring at −10° with 10.0 g (40.2 mmol) of (S)-6-chloro-3,11a-dihydro-5H-pyrrolo[2,1-c][1,4]benzodiazepine-5,11(10H)-dione, the mixture is stirred for 1 hour and subsequently 7.7 ml (44.6 mmol) of diethylchlorophosphate are added dropwise thereto at −35°.

Separately, 4.9 g (44.4 mmol) of potassium tert.butylate are dissolved in 15 ml of dry dimethylformamide, the solution is cooled in an acetone/dry-ice bath, treated with 6.31 g (44.6 mmol) of tert.butyl isocyanoacetate and the solution obtained is added dropwise at −15° to the mixture obtained according to the preceding paragraph. The resulting mixture is allowed to warm to 15°, neutralized with 2.5 of glacial acetic acid, poured into 150 ml of water and extracted three times with methylene chloride. The organic extracts are washed twice with water, dried over magnesium sulphate and evaporated. The crude product obtained is chromatographed on silica gel while eluting with ethyl acetate. After recrystallization from ethyl acetate/n-hexane, there is obtained tert.butyl 8-chloro-11,13a-dihydro-9-oxo-9H-imidazo[1,5-a]pyrrolo[2,1-c][1,4]benzodiazepine-1-carboxylate of melting point 227°–229°.

(c) 2.0 g (5.4 mmol) of tert.butyl 8-chloro-11,13a-dihydro-9-oxo-9H-imidazo[1,5-a]pyrrolo[2,1-c][1,4]benzodiazepine-1-carboxylate, 0.5 g (2.1 mmol) of tetraethyl orthotitanate and 25 ml of hydroxymethyl-cyclopropane are stirred at 130° for 23 hours, portions each of about 2 ml of solvent being distilled off in vacuo three times. The mixture is subsequently evaporated in vacuo, the residue is treated with water and chloroform, stirred for 30 minutes, filtered over siliceous earth and the organic phase is separated. The aqueous phase is extracted twice with chloroform, the organic extracts are washed once with saturated sodium chloride solution, dried over magnesium sulphate and evaporated. The crude product is chromatographed on silica gel while eluting with ethyl acetate. After recrystallization from ethyl acetate/n-hexane, there is obtained cyclopropylmethyl 8-chloro-11,13a-dihydro-9-oxo-9H-imidazo[1,5-a]pyrrolo[2,1-c][1,4]benzodiazepine-1-carboxylate of melting point 189°–190°.

EXAMPLE 12

4.51 g (10 mmol) of tert.butyl (S)-12,12a-dihydro-8-iodo-9-oxo-9H,11H-azeto[2,1-c]imidazo[1,5-a][1,4]benzodiazepine-1-carboxylate, 10.3 g (120 mmol) of hydroxymethyl-cyclobutane and 0.8 g (3 mmol) of tetrahydro orthotitanate are stirred at 130° for 2.5 hours, the solution is evaporated to dryness and the residue is taken up in chloroform. The solution obtained is stirred for 0.5 hour with 40 ml of a saturated potassium fluoride solution, the resulting emulsion is filtered through siliceous earth, the organic phase is separated, washed with water, dried over magnesium sulphate and evaporated. By crystallization from ethyl acetate there is obtained cyclobutylmethyl (S)-12,12a-dihydro-8-iodo-9-oxo-9H,11H-azeto[2,1-c]imidazo[1,5-a]benzodiazepine-1-carboxylate of melting point 169°–170°.

EXAMPLE 13

3.5 g (7.7 mmol) of tert.butyl (S)-12,12a-dihydro-8-iodo-9-oxo-9H,11H-azeto[2,1-c]imidazo[1,5-a][1,4]benzodiazepine-1-carboxylate, 10 g (116 mmol) of cyclopentanol and 0.8 g (3 mmol) of tetraethyl orthotitanate are stirred at 125° overnight, the solution obtained is evaporated and the residue is taken up in chloroform. The solution obtained is stirred for 0.5 hour with 40 ml of a saturated potassium fluoride solution, the resulting emulsion is filtered over siliceous earth, the organic phase is separated, washed with water, dried over magnesium sulphate and evaporated. By a rapid filtration through about 200 g of silica gel while eluting with ethyl acetate and subsequent crystallization from ethyl acetate there is obtained cyclopentyl (S)-12,12a-dihydro-8-iodo-9-oxo-9H,11H-azeto[2,1-c]imidazo[1,5-a][1,4]benzodiazepine-1-carboxylate of melting point 184°-185°.

EXAMPLE 14

(a) 25 g (103 mmol) of 6-bromo-isatoic acid anhydride and 10.44 g (103 mmol) of L-azetidine-2-carboxylic acid in 100 ml of dimethyl sulphoxide are stirred at 95° for 25 minutes, the dimethyl sulphoxide is removed in vacuo and the residue is heated to 150° for 3 hours in a high vacuum. By chromatography of the resulting material on silica gel while eluting with ethyl acetate and subsequent recrystallization from ethyl acetate there is obtained (S)-5-bromo-1,10a-dihydroazeto[2,1-c][1,4]benzodiazepine-4,10(2H,9H)-dione of melting point 182°-183°.

(b) A suspension of 19 g (67.3 mmol) of (S)-5-bromo-1,10a-dihydroazeto[2,1-c][1,4]benzodiazepine-4,10(2H,9H)-dione in 60 ml of dry dimethylformamide is treated while stirring at −20° with 1.75 g (73 mmol) of sodium hydride (55 percent oil dispersion, washed with n-hexane), the mixture is stirred at −20° for 20 minutes, then treated with 12.6 g (73 mmol) of diethylchlorophosphate and the mixture is stirred at this temperature for a further 0.5 hour.

Separately, 8.2 g (73 mmol) of potassium tert.butylate are dissolved in 20 ml of dry dimethylformamide, the solution is cooled in an acetone/dry-ice bath, treated with 10.3 g (73 mmol) of tert.butyl isocyanoacetate and the thus-obtained solution is added dropwise to the mixture obtained according to the preceding paragraph. The resulting mixture is allowed to warm to room temperature, poured into about 500 ml of water and stirred for a further 1 hour. The mixture is subsequently extracted three times with methylene chloride, the organic phase is washed twice with water, dried over magnesium sulphate and evaporated. By chromatography on silica gel while eluting with ethyl acetate and subsequent crystallization from ethyl acetate there is obtained tert.butyl (S)-8-bromo-12,12a-dihydro-9-oxo-9H,11H-azeto[2,1-c]imidazo[1,5-a][1,4]benzodiazepine-1-carboxylate of melting point 240°-241°.

(c) 8 g (20 mmol) of tert.butyl (S)-8-bromo-12,12a-dihydro-9-oxo-9H,11H-azeto[2,1-c]imidazo[1,5-a][1,4]benzodiazepine-1-carboxylate, 25 g (250 mmol) of cyclohexanol and 1.8 g (8 mmol) of tetraethyl orthotitanate are stirred at 120° overnight, the excess cyclohexanol is removed in a water-jet vacuum and the residue is taken up in chloroform. The solution obtained is stirred for 0.5 hour with 40 ml of a 1:1 mixture of concentrated hydrochloric acid and water, the organic phase is separated, washed once with 1N hydrochloric acid and once with saturated sodium bicarbonate solution, dried over magnesium sulphate and evaporated. By recrystallization from ethanol there is obtained cyclohexyl (S)-8-bromo-12,12a-dihydro-9-oxo-9H,11H-azeto[2,1-c]imidazo[1,5-a][1,4]benzodiazepine-1-carboxylate of melting point 203°-204°.

EXAMPLE 15

8 g (20 mmol) of tert.butyl (S)-8-bromo-12,12a-dihydro-9-oxo-9H,11H-azeto[2,1-c]imidazo[1,5-a][1,4]benzodiazepine-1-carboxylate, 25 g (300 mmol) of hydroxymethyl-cyclopropane and 1.8 g (8 mmol) of tetraethyl orthotitanate are stirred at 120° overnight, the solution is evaporated to dryness and the residue is taken up in chloroform. The solution obtained is stirred for 0.5 hour with 40 ml of a saturated potassium fluoride solution, the resulting emulsion is filtered through siliceous earth, the organic phase is separated, washed with water, dried over magnesium sulphate and evaporated. By recrystallization from ethanol there is obtained cyclopropylmethyl (S)-8-bromo-12,12a-dihydro-9-oxo-9H,11H-azeto[2,1-c]imidazo[1,5-a][1,4]benzodiazepine-1-carboxylate of melting point 212°-213°.

EXAMPLE 16

(a) 11.3 g (0.057 mol) of 6-chloro-isatoic acid anhydride and 5.78 g (0.057 mol) of L-azetidine-2-carboxylic acid are heated to 125° in 50 ml of dimethyl sulphoxide for 2 hours. The mixture is subsequently evaporated to dryness in a high vacuum and the residue obtained is heated to 150° for 2 hours. By chromatography on silica gel while eluting with ethyl acetate there is obtained (S)-5-chloro-1,10a-dihydroazeto[2,1-c][1,4]benzodiazepine-4,10(2H,9H)-dione of melting point 225°-228°.

(b) A suspension of 0.47 g (10.8 mmol) of sodium hydride (55 percent oil dispersion) in 10 ml of dry dimethylformamide is treated at −15° and while stirring with 2.12 g (9.0 mmol) of (S)-5-chloro-1,10a-dihydroazeto[2,1-c][1,4]benzodiazepine-4,10(2H,9H)-dione, the mixture is stirred for a further 1 hour and subsequently 1.8 ml (10.8 mmol) of diethylchlorophosphate are added dropwise at −35°.

Separately, 1.18 g (10.8 mmol) of potassium tert.butylate are dissolved in 8 ml of dry dimethylformamide, the solution is cooled in an acetone/dry-ice bath, treated with 1.52 g (10.8 mmol) of tert.butyl isocyanoacetate and the solution obtained is added dropwise at −15° to the mixture obtained according to the preceding paragraph. The resulting mixture is allowed to warm to 10°, neutralized with 0.6 ml of glacial acetic acid, poured into 80 ml of water and extracted three times with chloroform. The chloroform solution is washed twice with water, dried over magnesium sulphate and evaporated. The crude product obtained is chromatographed on silica gel while eluting with ethyl acetate and subsequently crystallized from ethyl acetate, there being obtained tert.butyl (S)-8-chloro-12,12a-dihydro-9-oxo-9H,11H-azeto[2,1-c]imidazo[1,5-a][1,4]benzodiazepine-1-carboxylate of melting point 235°-236°.

(c) 12.0 g (33.4 mmol) of tert.butyl (S)-8-chloro-12,12a-dihydro-9-oxo-9H,11H-azeto[2,1-c]imidazo[1,5-a][1,4]benzodiazepine-1-carboxylate, 3.4 g (13.6 mmol) of tetraethyl orthotitanate and 75 ml of cyclohexanol are stirred at 125° for 20 hours, a small amount of solvent being distilled off twice in vacuo. The mixture is subsequently evaporated in vacuo, the residue is dissolved in hot chloroform, treated with 200 ml of water and stirred for 30 minutes. The mixture is then filtered over siliceous earth, the organic phase is separated, the aqueous phase is extracted twice with chloroform, the organic extracts are dried over magnesium sulphate and evaporated. After chromatography on silica gel while eluting with ethyl acetate and subsequent recrystallization from ethyl acetate, there is obtained cyclohexyl (S)-8-chloro-12,12a-dihydro-9-oxo-9H,llH-azeto[2,1-c]imid.azo[1,5-a][1,4]benzodiazepine-1-carboxylate of melting point 223°–224°.

EXAMPLE 17

12 g (35 mmol) of ethyl (S)-8-chloro-11,12,13,13a-tetrahydro-9-oxo-9H-imidazo[1,5-a]pyrrolo[2,1-c][1,4]benzodiazepine-1-carboxylate and 1 g of powdered potassium cyanide in 120 ml of cyclohexanol are stirred at 130° for 18 hours, in each case about 10 ml of cyclohexanol being distilled off three times in the course of the reaction. The mixture is subsequently evaporated, the residue is taken up in chloroform, washed with water, dried over magnesium sulphate and evaporated. By column chromatography on silica gel there is obtained cyclohexyl (S)-8-chloro-11,12,13,13a-tetrahydro-9-oxo-9H-imidazo[1,5-a]pyrrolo[2,1-c][1,4]benzodiazepine-1-carboxylate of melting point 166°–167°.

EXAMPLE 18

(a) 15 g (43.4 mmol) of ethyl (S)-8-chloro-11,12,13,13a-tetrahydro-9-oxo-9H-imidazo[1,5-a]pyrrolo[2,1-c][1,4]benzodiazepine-1-carboxylate and 1.85 g (46.3 mmol) of sodium hydroxide are treated with 60 ml of ethanol and 10 ml of water, the mixture is then heated to boiling under reflux for 45 minutes, the ethanol is subsequently distilled off in vacuo, the mixture remaining is treated with 46.5 ml of 1N hydrochloric acid and left to stand in an ice-bath for 2 hours. The precipitated material is filtered off under suction, washed with water and dried up to constant weight. There is obtained (S)-8-chloro-11,12,13,13a-tetrahydro-9-oxo-9H-imidazo[1,5-a]pyrrolo[2,1-c][1,4]benzodiazepine-1-carboxylic acid having a decomposition point of 265°.

(b) 9.54 g (30 mmol) of (S)-8-chloro-11,12,13,13a-tetrahydro-9-oxo-9H-imidazo[1,5-a]pyrrolo[2,1-c][1,4]benzodiazepine-1-carboxylic acid and 6.32 g (39 mmol) of N,N'-carbonyldiimidazole in 50 ml of dry dimethylformamide are stirred at room temperature for 1 hour and at 50° for 1 hour. The mixture is subsequently poured into about 300 ml of water, the precipitated material is filtered off under suction, washed with water and dried up to constant weight. There is obtained (S)-1-[(8-chloro-11,12,13,13a-tetrahydro-9-oxo-9H-imidazo[1,5-a]pyrrolo[2,1-c][1,4]benzodiazepin-1-yl)carbonyl]imidazole of melting point 240°–241.5°.

(c) A mixture of 601 mg (6 mmol) of cyclohexanol, 10 ml of dimethylformamide and 288 mg (6 mmol) of sodium hydride (55 percent oil dispersion) is stirred at room temperature for 0.5 hour, the solution obtained is treated with 2.20 g (6 mmol) of (S)-1-[(8-chloro-11,12,13,13a-tetrahydro-9-oxo-9H-imidazo[1,5-a]pyrrolo[2,1-c][1,4]benzodiazepin-1-yl)carbonyl]imidazole, the mixture is stirred at room temperature for a further 0.5 hour and then poured into about 70 ml of water. The precipitated material is filtered off under suction, washed with water and dried. By recrystallization from ethyl acetate there is obtained cyclohexyl (S)-8-chloro-11,12,13,13a-tetrahydro-9-oxo-9H-imidazo[1,5-a]pyrrolo[2,1-c][1,4]benzodiazepine-1-carboxylate of melting point 166°–167°.

EXAMPLE 19

3.45 g (10 mmol) of ethyl (S)-8-chloro-11,12,13,13a-tetrahydro-9-oxo-9H-imidazo[1,5-a]pyrrolo[2,1-c][1,4]benzodiazepine-1-carboxylate and 70 mg of powdered potassium cyanide in 10 ml of cyclopentanol are stirred at the boiling point overnight, the excess cyclopentanol is removed in vacuo, the residue is taken up in chloroform, filtered and evaporated. By recrystallization from ethyl acetate/hexane there is obtained cyclopentyl (S)-8-chloro-11,12,13,13a-tetrahydro-9-oxo-9H-imidazo[1,5-a]pyrrolo[2,1-c][1,4]benzodiazepine-1-carboxylate of melting point 210.5°–212°.

EXAMPLE 20

10.35 g (0.03 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 25 ml of hydroxymethylcyclobutane and 0.5 g of powdered potassium cyanide are heated to 165° for 2 hours, the ethanol formed being distilled off continuously. The mixture is subsequently evaporated in vacuo, the residue is taken up in chloroform, the chloroform solution is washed three times with water, dried over magnesium sulphate and evaporated. By recrystallization of the resulting material from ethyl acetate there is obtained cyclobutylmethyl (S)-8-chloro-11,12,13,13a-tetrahydro-9-oxo-9H-imidazo[1,5-a]pyrrolo[2,1-c][1,4]benzodiazepine-1-carboxylate of melting point 204°–205°.

EXAMPLE 21

A mixture of 1.84 g (5 mmol) of (S)-1-[(8-chloro-11,12,13,13a-tetrahydro-9-oxo-9H-imidazo[1,5-a]pyrrolo[2,1-c][1,4]benzodiazepin-1-yl)carbonyl]imidazole, 0.56 g (6 mmol) of phenol, 0.83 g (6 mmol) of powdered potassium carbonate and 20 ml of dry dimethylformamide is stirred at room temperature for 26 hours, then poured into 100 ml of water and extracted three times with chloroform. The chloroform solution is washed twice with water and three times with saturated sodium chloride solution, dried over magnesium sulphate and evaporated. The crude product is purified by chromatography on silica gel while eluting with ethyl acetate and recrystallization from ethyl acetate. There is obtained phenyl (S)-8-chloro-11,12,13,13a-tetrahydro-9-oxo-9H-imidazo[1,5-a]pyrrolo[2,1-c][1,4]benzodiazepine-1-carboxylate of melting point 211°–212°.

EXAMPLE 22

(a) A solution of 7.03 g (30 mmol) of (S)-7-fluoro-1,2,3,11a-tetrahydro-5H-pyrrolo[2,1-c][1,4]benzodiazepine-5,11(10H)-dione in 50 ml of dry dimethylformamide is treated while stirring at −25° with 1.51 g (34.5 mmol) of sodium hydride (55 percent oil dispersion), the mixture is stirred at −20° to −10° for a further 50 minutes and subsequently 9.1 ml (34.5 mmol) of diethylchlorophosphate are added dropwise at −40°.

Separately, 3.86 g (34.5 mmol) of potassium tert.butylate are dissolved in 10 ml of dry dimethylformamide, the solution is cooled in an acetone/dry-ice bath, treated with 4.86 g (34.5 mmol) of tert.butyl isocyanoacetate and the thus-obtained solution is added dropwise at −15° to the mixture obtained according to the preceding paragraph. The resulting mixture is allowed to warm to 5°, neutralized with 3.9 ml of glacial acetic acid, poured into 250 ml of water and stirred for a further 0.5 hour. The mixture is then extracted three times with methylene chloride, the organic solution is washed twice with water, dried over magnesium sulphate and the solvent is removed by distillation. The crude product obtained is chromatographed on silica gel while eluting with ethyl acetate. By crystallization from ethanol there is obtained tert.butyl (S)-7-fluoro-11,12,13,13a-tetrahydro-9-oxo-9H-imidazo[1,5-a]pyrrolo[2,1-c][1,4]benzodiazepine-1-carboxylate of melting point 154°–155°.

(b) 11.85 g (33.2 mmol) of tert.butyl (S)-7-fluoro-11,12,13,13a-tetrahydro-9-oxo-9H-imidazo[1,5-a]pyrrolo[2,1-c]benzodiazepine-1-carboxylate, 30 g (400 mmol) of hydroxymethyl-cyclopropane and 6 ml of tetraethyl orthotitanate are stirred at 115° overnight, whereupon the mixture is evaporated and the residue is dissolved in chloroform. The solution is stirred for 0.5 hour with about 40 ml of a saturated potassium fluoride solution, the mixture is filtered through siliceous earth and the organic phase is separated. The organic phase is washed with water, dried over magnesium sulphate and evaporated. By chromatography on a silica gel column and subsequent crystallization from ethyl acetate there is obtained cyclopropylmethyl (S)-7-fluoro-11,12,13,13a-tetrahydro-9-oxo-9H-imidazo[1,5-a]pyrrolo[2,1-c][1,4]benzodiazepine-1-carboxylate of melting point 140°–142°.

EXAMPLE 23

13.0 g (128.4 mmol) of L-azetidine-2-carboxylic acid and 22.7 g (128.4 mmol) of 6-methyl-isatoic acid anhydride in 150 ml of dimethyl sulphoxide are heated to 95° for 3 hours, evaporated to dryness in a high vacuum and the residue obtained is heated to 140° for 2.25 hours. By crystallization from ethyl acetate there is obtained (S)-1,10a-dihydro-5-methyl-2H-azeto[2,1-c][1,4]benzodiazepine-4,10(9H)-dione of melting point 159°–160°.

(b) A solution of 13.8 g (63.8 mmol) of (S)-1,10a-dihydro-5-methyl-2H-azeto[2,1-c][1,4]benzodiazepine-4,10(9H)-dione in 55 ml of dry dimethylformamide is treated at −20° to −10° while stirring with 3.06 g (70.2 mmol) of sodium hydride (55 percent oil dispersion), the mixture is stirred at the above temperature for a further 40 minutes and subsequently 10.5 ml (70.2 mmol) of diethylchlorophosphate are added dropwise at −35°.

Separately, 7.88 g (70.2 mmol) of potassium tert.butylate are dissolved in 12 ml of dry dimethylformamide, the solution is cooled in an acetone/dry-ice bath, treated with 11 g (70.2 mmol) of about 90 percent tert.butyl isocyanoacetate and the solution obtained is added dropwise at −20° to −15° to the mixture obtained according to the preceding paragraph. The resulting mixture is allowed to warm to 0°, neutralized with 4 ml of glacial acetic acid, poured into 300 ml of water and extracted three times with methylene chloride. The methylene chloride solution is washed twice with water, dried over magnesium sulphate and evaporated. The crude product obtained is chromatographed on silica gel while eluting with ethyl acetate containing 50% n-hexane. After recrystallization from ethyl acetate/n-hexane, there is obtained tert.-butyl (S)-12,12a-dihydro-8-methyl-9-oxo-9H,11H-azeto[2,1-c]imidazo[1,5-a][1,4]benzodiazepine-1-carboxylate of melting point 191°–192°.

(c) 3.39 g (10 mmol) of tert.butyl (S)-12,12a-dihydro-8-methyl-9-oxo-9,11H-azeto[2,1-c]imidazo[1,5-a][1,4]benzodiazepine-1-carboxylate, 50 ml of cyclohexanol and 1 g of tetraethyl orthotitanate are heated to 130° for 16 hours, a small amount of solvent being distilled off after 2 hours and after 4 hours. The mixture is subsequently evaporated in vacuo, the residue is dissolved in chloroform and poured into water. After filtration through siliceous earth, the chloroform phase is separated, dried over magnesium sulphate and evaporated. By crystallization from ethyl acetate there is obtained cyclohexyl (S)-12,12a-dihydro-8-methyl-9-oxo-9H,11H-azeto[2,1-c]imidazo[1,5-a][1,4]benzodiazepine-1-carboxylate of melting point 199°–200°.

EXAMPLE 24

5 g (14.5 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 70 mg of powdered potassium cyanide and 20 ml of benzyl alcohol are stirred at 110° for 1 hour, evaporated to dryness and the residue is taken up in chloroform. The solution is washed with water, dried over magnesium sulphate and evaporated. By recrystallization from ethanol and ether there is obtained benzyl (S)-8-chloro-11,12,13,13a-tetrahydro-9-oxo-9H-imidazo[1,5-a]pyrrolo[2,1-c][1,4]benzodiazepine-1-carboxylate of melting point 141°–142°.

EXAMPLE 25

1.2 g (12 mmol) of 1-methyl-cyclopentanol in 25 ml of dry dimethylformamide is treated with 0.5 g (10.3 mmol) of sodium hydride (55% oil dispersion) and to the resulting solution there are added portionwise at −20° 3.79 g (10.3 mmol) of (S)-1-[(8-chloro-11,12,13,13a-tetrahydro-9-oxo-9H-imidazo[1,5-a]pyrrolo[2,1-c][1,4]benzodiazepin-1-yl)carbonyl]imidazole. The mixture is stirred at room temperature for 1 hour, poured into about 250 ml of water, the precipitated material is filtered off under suction, washed with water and dried. There is obtained 1-methyl-cyclopentyl 8-chloro-11,12,13,13a-tetrahydro-9-oxo-9H-imidazo[1,5-a]pyrrolo[2,1-c][1,4]benzodiazepine-1-carboxylate of melting point 190°–191°.

EXAMPLE 26

3.19 g (10 mmol) of ethyl 7-chloro-5,6-dihydro-5-methyl-6-oxo-4H-imidazo[1,5-a][1,4]benzodiazepine-3-carboxylate, 70 mg of powdered potassium cyanide and 10 ml of cyclopentanol are stirred at 120° overnight, subsequently evaporated and the residue is chromatographed on silica gel while eluting with ethyl acetate. By recrystallization from ethyl acetate there is obtained cyclopentyl 7-chloro-5,6-dihydro-5-methyl-6-oxo-4H-imidazo[1,5-a][1,4]benzodiazepine-3-carboxylate of melting point 162°–163°.

EXAMPLE 27

A mixture of 6.92 g (0.02 mol) of ethyl (S)-8-chloro-11,12,13,13a-tetrahydro-9-oxo-9H-imidazo[1,5-a]pyrrolo[2,1-c][1,4]benzodiazepine-1-carboxylate, 100 ml of propargyl alcohol and 0.4 g of potassium cyanide is heated to boiling under reflux for 4 hours, 75 ml of the solvent are then removed by distillation, 75 ml of propargyl alcohol are added to the mixture and the resulting mixture is heated to boiling under reflux for a further 16 hours. The mixture is concentrated, 25 ml of water are added to the residue and the mixture obtained is extracted three times with 25 ml of chloroform each time, the chloroform solution is dried over magnesium sulphate and evaporated. The residue is chromatographed on silica gel while eluting with ethyl acetate. By recrystallization from ethyl acetate there is obtained 2-propynyl (S)-8-chloro-11,12,13,13a-tetrahydro-9-oxo- 9H-imidazo[1,5-a]pyrrolo[2,1-c][1,4]benzodiazepine-1-carboxylate of melting point 213°–214°.

EXAMPLE 28

A mixture of 6.9 g (20 mmol) of ethyl (S)-8-chloro-11,12,13,13a-tetrahydro-9-oxo-9H-imidazo[1,5-a]pyrrolo[2,1-c][1,4]-benzodiazepine-1-carboxylate, 0.6 g (9.2 mmol) of potassium cyanide and 70 ml of hydroxymethyl-cyclohexane is stirred at 130° for 16 hours, a small amount of solvent being distilled off twice in the course of the reaction. The mixture is subsequently evaporated in a high vacuum, the residue is partitioned between water and chloroform, the chloroform solution is washed twice with saturated sodium chloride solution and dried over magnesium sulphate. After evaporation of the chloroform solution, the residue is crystallized from ethyl acetate/n-hexane, there being obtained cyclohexylmethyl (S)-8-chloro-11,12,13,13a-tetrahydro-9-oxo-9H-imidazo[1,5-a]pyrrolo[2,1-c][1,4]benzodiazepine-1-carboxylate of melting point 123°–124° C.

EXAMPLE 29

A mixture of 6.9 g (20 mmol) of ethyl (S)-8-chloro-11,12,13,13a-tetrahydro-9-oxo-9H-imidazo[1,5-a]pyrrolo2,1-c][1,4]benzodiazepine-1-carboxylate, 0.6 g (9.3 mmol) of potassium cyanide and 30 ml of cyclopentanemethanol is stirred at 130° for 26 hours, a small amount of solvent being distilled off in vacuo twice. The mixture is subsequently evaporated in a high vacuum, the residue is partitioned between water and chloroform and the aqueous phase is extracted once more with chloroform. The organic extracts are washed three times with saturated sodium chloride solution, dried over magnesium sulphate and evaporated. The residue is taken up in boiling ethyl acetate, filtered and evaporated. After crystallization of the residual oil from ethyl acetate/n-hexane, there is obtained cyclopentylmethyl (S)-8-chloro-11,12,13,13a-tetrahydro-9-oxo-9H-imidazo[1,5-a]pyrrolo[2,1-c][1,4]benzodiazepine-1-carboxylate of melting point 112°–114°.

EXAMPLE 30

A mixture of 3.45 (10 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 11.4 g (100 mmol) of trans-2-methylcyclohexanol and 100 mg of powdered potassium cyanide is stirred at 130° for 6 hours, the solution obtained is evaporated to dryness and the residue is chromatographed on a silica gel column. By recrystallization from ethyl acetate there is obtained trans-2-methylcyclohexyl (S)-8-chloro-11,12,13,13a-tetrahydro-9-oxo-9H-imidazo[1,5-a]pyrrolo[2,1-c][1,4]benzodiazepine-1-carboxylate of melting point 213°–215° (1:1 mixture of the two diastereoisomers).

EXAMPLE 31

A mixture of 3.45 g (10 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 100 mg of powdered potassium cyanide and 10 g (100 mmol) of tetrahydro-2H-pyran-4-ol is heated at 140° for 20 hours, whereupon the excess tetrahydro-2H-pyran-4-ol is distilled off and the residue is taken up in chloroform. The solution is washed with water, dried over magnesium sulphate and evaporated. By crystallization from ethyl acetate there is obtained tetrahydro-2H pyran-4-yl (S)-8-chloro-11,12,13,13a-tetrahydro-9-oxo-9H-imidazo[1,5-a]pyrrolo[2,1-c][1,4]benzodiazepine-1-carboxylate of melting point 226°–227°.

EXAMPLE 32

A mixture of 20.0 g (62.5 mmol) of ethyl 7-chloro-5,6-dihydro-5-methyl-6-oxo-4H-imidazo[1,5-a][1,4]benzodiazepine-3-carboxylate, 1.0 g (15.4 mmol) of potassium cyanide and 100 ml of propargyl alcohol is stirred at 130° for 40 hours, about 50 ml of solvent being distilled off in vacuo after 16 hours and 50 ml of propargyl alcohol being added to the mixture. The mixture is subsequently evaporated to dryness in vacuo, the residue is taken up in chloroform, the chloroform solution is washed once with water and once with saturated sodium chloride solution and dried over magnesium sulphate. The magnesium sulphate is removed by filtration under suction and the chloroform solution is filtered through silica gel, elution being subsequently carried out with ethyl acetate. After evaporation of the eluate, the residue is recrystallized twice from chloroform/toluene and once from ethanol, there being obtained 2-propynyl 7-chloro-5,6-dihydro-5-methyl-6-oxo-4H-imidazo[1,5-a][1,4]benzodiazepine-3-carboxylate of melting point 198°–200°.

EXAMPLE 33

A mixture of 20.0 g (65.9 mmol) of ethyl 8-fluoro-5,6-dihydro-5-methyl-6-oxo-4H-imidazo[1,5-a][1,4]benzodiazepine-3-carboxylate, 1.0 g (15.4 mmol) of potassium cyanide and 100 ml of propargyl alcohol is stirred at 125° for 20 hours and at 135° for 1 hour, evaporated to dryness in vacuo and the residue is taken up in chloroform. The chloroform solution is washed twice with water, dried over magnesium sulphate and evaporated. The residue is chromatographed on silica gel while eluting with ethyl acetate. By recrystallization of the resulting material from chloroform/toluene there is obtained 2-propynyl 8-fluoro-5,6-dihydro-5-methyl-6-oxo-4H-imidazo[1,5-a][1,4]benzodiazepine-3-carboxylate of melting point 220°–222°.

EXAMPLE 34

A mixture of 5.0 g (15.6 mmol) of ethyl 7-chloro-5,6-dihydro-5-methyl-6-oxo-4H-imidazo[1,5-a][1,4]benzodiazepine-3-carboxylate, 20 ml of hydroxymethylcyclopropane and 0.5 g of powdered potassium cyanide is heated to 130° for 18 hours, about 1 ml of solvent being distilled off after 1.3 hours and after 6 hours. The mixture is subseqently evaporated in vacuo and the residue is partitioned between chloroform and water. The chloroform phase is washed three times with water, dried over magnesium sulphate and evaporated. The material obtained is chromatographed on silica gel while eluting with ethyl acetate and subsequently crystallized from ethyl acetate. There is obtained cyclopropylmethyl 7-chloro-5,6-dihydro-5-methyl-6-oxo-4H-imidazo[1,5-a][1,4]benzodiazepine-3-carboxylate of melting point 194°–195°.

EXAMPLE 35

(a) 4,5-Dichloroisatin is obtained from 3,4-dichloroaniline according to the Sandmeyer isatin synthesis [T. Sandmeyer, Helv. 2, 234 (1919)]. Separation of the isomers according to P. W. Sadler, J. Org. Chemistry 21, 169 (1956) yields, after recrystallization, pure 4,5-dichloroisatin of melting point 227°–230°.

(b) 49 g (0.226 mol) of 4,5-dichloroisatin are suspended in 200 ml of acetic acid and 200 ml of acetic anhydride, treated over a period of 50 minutes at a temperature between 80° and 90° with 37.65 g (0.376 mol) of chromium trioxide and the mixture is subsequently cooled to 5°. The precipitated material is filtered off under suction, washed with water and dried. There is obtained 5,6-dichloroisatoic acid anhydride of melting point 280°–283°.

(c) A mixture of 22 g (94.8 mmol) of 5,6-dichloroisatoic acid anhydride, 10.85 g (94.8 mmol) of L-proline and 100 ml of dimethyl sulphoxide is heated to 90° for 0.5 hour, subsequently evaporated to dryness in a high vacuum and the residue is heated to 150° for 1 hour. By chromatography on silica gel while eluting with ethyl acetate and subsequent crystallization from ethyl acetate and hexane there is obtained (S)-6,7-dichloro-1,2,3,11a-tetrahydro-5H-pyrrolo[2,1-c][1,4]benzodiazepine-5,11(10H)-dione of melting point 203°–205° C.

(d) A suspension of 21 g (73.6 mmol) of (S)-6,7-dichloro-1,2,3,11a-tetrahydro-5H-pyrrolo[2,1-c][1,4]benzodiazepine-5,11(10H)-dione in 60 ml of dry dimethylformamide is treated while stirring at −30° with 3.20 g (85 mmol) of sodium hydride (55 percent oil dispersion), the mixture is stirred at −20° for 0.5 hour and subsequently 14.67 g (85 mmol) of diethylchlorophosphate are added dropwise.

Separately, 9.53 g (85 mmol) of potassium tert.butylate are dissolved in 30 ml of dry dimethylformamide, the solution is cooled in an acetone/dry-ice bath, treated with 12 g (85 mmol) of tert.butyl isocyanoacetate and the thus-obtained solution is added dropwise at −15° to the mixture obtained according to the preceding paragraph. The resulting mixture is allowed to warm to room temperature, poured into 400 ml of water and stirred for a further 1 hour. The mixture is extracted three times with methylene chloride, the organic phase is washed twice with water, dried over magnesium sulphate and the solvent is removed by distillation. The crude product obtained is chromatographed on silica gel while eluting with ethyl acetate and subsequently recrystallized from ethyl acetate, there being obtained tert.butyl (S)-7,8-dichloro-11,12,13,13a-tetrahydro-9-oxo-9H-imidazo[1,5-a]pyrrolo[2,1-c][1,4]benzodiazepine-1-carboxylate of melting point 213°–214°.

(e) A mixture of 4.0 g (7.3 mmol) of tert.butyl (S)-7,8-dichloro-11,12,13,13a-tetrahydro-9-oxo-9H-imidazo[1,5-a]pyrrolo[2,1-c][1,4]benzodiazepine-1-carboxylate, 10 ml (126 mmol) of hydroxymethyl-cyclopropane and 1 g (3 mmol) of tetraethyl orthotitanate is stirred at 125° overnight, the mixture is evaporated and the residue is taken up in chloroform. The solution is stirred for 0.5 hour with 30 ml of a saturated potassium fluoride solution and the mixture is filtered through siliceous earth. The organic phase is separated, washed with water, dried over magnesium sulphate and evaporated. By crystallization from ethyl acetate there is obtained cyclopropylmethyl (S)-7,8-dichloro-11,12,13,13a-tetrahydro-9-oxo-9H-imidazo[1,5-a]pyrrolo[2,1-c][1,4]benzodiazepine-1-carboxylate of melting point 185°–186°.

EXAMPLE 36

6.92 g (20 mmol) of ethyl (S)-7-chloro-11,12,13,13a-tetrahydro-9-oxo-9H-imidazo[1,5-a]pyrrolo[2,1-c][1,4]benzodiazepine-1-carboxylate, 20 g of hydroxymethyl-cyclopropane and 1 g of tetraethyl orthotitanate are heated to 130° for 16 hours, evaporated in vacuo, the residue is taken up in chloroform and the solution is poured into about 20 percent hydrochloric acid. The mixture is stirred for 20 minutes, the chloroform phase is separated, washed successively with 1N hydrochloric acid and saturated sodium bicarbonate solution, dried over magnesium sulphate and evaporated. By crystallization from ethyl acetate there is obtained cyclopropylmethyl (S)-7-chloro-11,12,13,13a-tetrahydro-9-oxo-9H-imidazo[1,5-a]pyrrolo[2,1-c][1,4]benzodiazepine-1-carboxylate of melting point 146°–148°.

EXAMPLE 37

A mixture of 17.29 g (50 mmol) of ethyl (S)-8-chloro-11,12,13,13a-tetrahydro-9-oxo-9H-imidazo[1,5-a]pyrrolo[2,1-C][1,4]benezodiazepine-1-carboxylate, 1.0 g (15.4 mmol) of potassium cyanide and 50 ml of 3-methyl-cyclohexanol (mixture of the cis and trans isomers) is heated at 140° for 25 hours, 20 ml of solvent being distilled off after 5 hours and after 16 hours and a further 25 ml of 3-methyl-cyclohexanol being added to the mixture. The mixture is subsequently evaporated in vacuo, the residue is taken up in 300 ml of chloroform, the chloroform solution is washed once with water, dried over magnesium sulphate and evaporated. The residue is chromatographed on silica gel while eluting with ethyl acetate/n-hexane (1:1) and the two substances obtained are subsequently recrystallized from ethyl acetate/n-hexane.

There are obtained (rac)-trans-3-methylcyclohexyl (S)-8-chloro-11,12,13,13a-tetrahydro-9-oxo-9H-imidazo[1,5-a]pyrrolo[2,1-c][1,4]benzodiazepine-1-carboxylate as a (1:1) mixture of the two diastereomers of melting point 130°–142° and having the largest Rf value; and (rac)-cis-3-methylcyclohexyl (S)-8-chloro-11,12,13,13a-tetrahydro-9-oxo-9H-imidazo[1,5-a]pyrrolo[2,1-c][1,4]benzodiazepine-1-carboxylate as a (1:1) mixture of the two diastereomers of melting point 142°–160° and having the smallest Rf value.

EXAMPLE 38

A mixture of 3.45 g (10 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 0.8 g (3 mmol) of tetraethyl orthotitanate and 10 g (102 mmol) of 2-cyclohexen-1-ol is stirred at 120° overnight, evaporated to dryness and the residue is taken up in chloroform. The resulting solution is stirred with about 30 ml of saturated potassium fluoride solution, filtered through siliceous earth, the organic phase is separated, washed with water, dried over magnesium sulphate and evaporated. By chromatography on silica gel while eluting with ethyl acetate and subsequent recrystallization from ethyl acetate and hexane there is obtained (R,S)-2-cyclohexen-1-yl (S)-8-chloro-11,12,13,13a-tetrahydro-9-oxo-9H-imidazo[1,5-a]pyrrolo[2,1-c][1,4]benzodiazepine-1-carboxylate of melting point 179°–180°.

EXAMPLE 39

A mixture of 10.35 g (30 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 50 g of cycloheptanol and 2 g of tetraethyl orthotitanate is heated to 130° for 8 hours, evaporated in vacuo, the residue is taken up in chloroform and the solution obtained is poured into about 20 percent hydrochloric acid. The mixture is stirred for 15 minutes, the chloroform phase is separated, washed successively with 2N hydrochloric acid and saturated sodium bicarbonate solution, dried over magnesium sulphate and evaporated. By crystallization from ethyl acetate/hexane there is obtained cycloheptyl (S)-8-chloro-11,12,13,13a-tetrahydro-9-oxo-9H-imidazo[1,5-a]pyrrolo[2,1-c][1,4]benzodiazepine-1-carboxylate of melting point 179°–180°.

EXAMPLE 40

A mixture of 10.35 g (0.03 mmol) of ethyl (S)-8-chloro-11,12,13,13a-tetrahydro-9-oxo-9H-imidazo[1,5-a]pyrrolo[2,1-c][1,4]benzodiazepine-1 carboxylate, 50 g of cyclooctanol and 2 g of tetraethyl orthotitanate is heated to 130° for 8 hours, a small amount of solvent being distilled off twice in vacuo. The mixture is subsequently evaporated in vacuo, the residue is taken up in chloroform and the solution is poured into about 20 percent hydrochloric acid. The mixture is stirred for 20 minutes, the chloroform phase is separated, washed successively with 1N hydrochloric acid and saturated sodium bicarbonate solution, dried over magnesium sulphate and evaporated. By chromatography on a silica gel column while eluting with ethyl acetate and subsequent crystallization from ethyl acetate/hexane there is obtained cyclooctyl (S)-8-chloro-11,12,13,13a-tetrahydro-9-oxo-9H-imidazo[1,5-a]pyrrolo[2,1-c][1,4]benzodiazepine-1-carboxylate of melting point 183°–184°.

EXAMPLE 41

A mixture of 6.93 g (0.02 mmol) of ethyl (S)-8-chloro-11,12,13,13a-tetrahydro-9-oxo-9H-imidazo[1,5-a]pyrrolo[2,1-c][1,4]benzodiazepine-1-carboxylate 1.4 g of tetraethyl orthotitanate and 24 g of 2-cyclohexylethanol is heated to 140° for 2.5 hours, evaporated in vacuo, the residue is taken up in chloroform and the solution is poured into about 20 percent hydrochloric acid. The mixture is stirred for 15 minutes, the chloroform phase is separated, washed successively with 2N hydrochloric acid and saturated sodium bicarbonate solution, dried over magnesium sulphate and evaporated. After chromatography on a silica gel column while eluting with ethyl acetate and subsequent crystallization from ethyl acetate/hexane, there is obtained 2-cyclohexylethyl (S)-8-chloro-11,12,13,13a-tetrahydro-9-oxo-9H-imidazo[1,5-a]pyrrolo[2,1-c][1,4]benzodiazepine-1-carboxylate of melting point 131°–132°.

EXAMPLE 42

A mixture of 8.72 g (27 mmol) of ethyl-7-chloro-5,6-dihydro-5-methyl-6-oxo-4H-imidazo[1,5-a][1,4]benzodiazepine-3-carboxylate, 2 g (9 mmol) of tetraethyl orthotitanate and 27 g (270 mmol) of cyclohexanol is stirred at 125° overnight, evaporated to dryness, the residue is taken up in chloroform, the chloroform solution is washed successively with 40 ml of 5N hydrochloric acid and saturated sodium bicarbonate solution, dried over magnesium sulphate and evaporated. By recrystallization from ethanol and ether there is obtained cyclohexyl 7-chloro-5,6-dihydro-5-methyl-6-oxo-4H-imidazo[1,5-a][1,4]benzodiazepine-3-carboxylate of melting point 208°–209°.

EXAMPLE 43

A mixture of 3.45 g (10 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 100 mg of powdered potassium cyanide and 14.20 g (100 mmol) of 2-chlorobenzyl alcohol is stirred at 130° for 90 hours, the mixture is diluted with about 30 ml of methylene chloride and chromatographed on about 300 g of silica gel while eluting with ethyl acetate. By recrystallization from ethyl acetate there is obtained o-chlorobenzyl (S)-8-chloro-11,12,13,13a-tetrahydro-9-oxo-9H-imidazo[1,5-a]pyrrolo[2,1-c][1,4]benzodiazepine-1-carboxylate of melting point 192°–193°.

EXAMPLE 44

A mixture of 3.45 g (10 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 100 mg of powdered potassium cyanide and 14.2 g of 3-chlorobenzyl alcohol is stirred at 130° for 48 hours, the mixture is diluted with about 20 ml of methylene chloride and chromatographed on about 300 g of silica gel while eluting with ethyl acetate. By crystallization from ethyl acetate and hexane there is obtained m-chlorobenzyl (S)-8-chloro-11,12,13,13a-tetrahydro-9-oxo-9H-imidazo[1,5-a]pyrrolo[2,1-c][1,4]benzodiazepine-1-carboxylate of melting point 114°–116°.

EXAMPLE 45

A mixture of 3.45 g (10 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 100 mg of powdered potassium cyanide and 9.90 g of 4-chlorobenzyl alcohol is heated at 130° for 48 hours, the mixture is diluted with about 20 ml of methylene chloride and chromatographed on about 300 g of silica gel while eluting with ethyl acetate. By recrystallization from ethyl acetate there is obtained p-chlorobenzyl (S)-8-chloro-11,12,13,13a-tetrahydro-9-oxo-9H-imidazo[1,5-a]pyrrolo[2,1-c][1,4]benzodiazepine-1-carboxylate of melting point 183°–184°.

EXAMPLE 46

A mixture of 3.45 g (10 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 100 mg (1.5 mmol) of potassium cyanide and 20 ml of 2-methoxybenzyl alcohol is stirred at 110° for 36 hours, the resulting ethanol being removed in vacuo from time to time. The solvent is subsequently removed by distillation in a high vacuum and the residue is chromatographed on silica gel while eluting with ethyl acetate. By recrystallization from ethyl acetate/n-hexane there is obtained o-methoxybenzyl (S)-8-chloro-11,12,13,13a-tetrahydro-9-oxo-9H-imidazo[1,5-a]pyrrolo[2,1-c][1,4]benzodiazepine-1-carboxylate of melting point 178°–179°.

EXAMPLE 47

A mixture of 3.45 g (10 mmol) of ethyl (S)-8-chloro-11,12,13,13a-tetrahydro-9-oxo-9H-imidazo[1,5-a]pyrrolo[1,2-c][1,4]benzodiazepine-1-carboxylate, 100 mg (1.5 mmol) of potassium cyanide and 20 ml of 3-methoxybenzyl alcohol is stirred at 110° for 36 hours, the resulting ethanol being removed in vacuo from time to time. The solvent is subsequently removed by distillation in a high vacuum, the residue is taken up in chloroform, the chloroform solution is washed three times with water, dried over magnesium sulphate and evaporated. The crude product is chromatographed on silica gel while eluting with ethyl acetate. By crystallization from ethyl acetate/n-hexane there is obtained m-methoxybenzyl (S)-8-chloro-11,12,13,13a-tetrahydro-9- oxo-9H-imidazo[1,5-a]pyrrolo[2,1-c][1,4]benzodiazepine-1-carboxylate of melting point 131°–133°.

EXAMPLE 48

A mixture of 3.45 g (10 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 100 mg (1.5 mmol) of potassium cyanide and 20 ml of 4-methoxybenzyl alcohol is stirred at 110° for 3.5 days, the resulting ethanol being removed in vacuo from time to time. The solvent is subsequently removed by distillation in a high vacuum, the residue is taken up in methylene chloride, the methylene chloride solution is washed three times with water, dried over magnesium sulphate and evaporated. The crude product is chromatographed on silica gel while eluting with ethyl acetate. By recrystallization from ethyl acetate there is obtained p-methoxybenzyl (S)-8-chloro-11,12,13,13a-tetrahydro-9-oxo-9H-imidazo[1,5-a]pyrrolo[2,1-c][1,4]benzodiazepine-1-carboxylate of melting point 185°–186°.

EXAMPLE 49

A mixture of 3.59 g (10 mmol) of tert.butyl (S)-8-chloro-12,12a-dihydro-9-oxo-9H,11H-azeto[2,1-c]imidazo[1,5-a][1,4]benzodiazepine-1-carboxylate, 1.5 g (6 mmol) of tetraethyl orthotitanate and 30 ml of benzyl alcohol is stirred at 130° for 6 hours, a small amount of solvent being distilled off in vacuo twice. The mixture is subsequently evaporated in a high vacuum, the residue is taken up in 40 ml of chloroform, the solution is treated with 40 ml of concentrated hydrochloric acid/water (1:1) and the mixture is stirred until both phases are clear. The chloroform solution is washed successively with 20 ml of 1N hydrochloric acid and saturated sodium bicarbonate solution, dried over magnesium sulphate and evaporated to dryness. The residue is crystallized from ethyl acetate and there is obtained benzyl (S)-8-chloro-12,12a-dihydro-9-oxo-9H,11H-azeto[2,1-c]imidazo[1,5-a][1,4]benzodiazepine-1-carboxylate of melting point 180°–182°.

By chromatography of the mother liquor on silica gel while eluting with ethyl acetate and subsequent recrystallization from ethyl acetate there is obtained a second portion of the desired substance having the same purity.

EXAMPLE 50

(a) 10.6 g (50.9 mmol) of 6-nitro-isatoic acid anhydride and 6.1 g (50.9 mmol) of L-proline in 70 ml of dimethyl sulphoxide are heated to 90° for 45 minutes, subsequently evaporated in a high vacuum and the residue obtained is heated to 140° for 4 hours. The crystalline crude product is taken up in 100 ml of boiling ethanol, left to stand in the cold overnight, the material obtained in filtered off under suction while washing with cold ethanol and dried up to constant weight. There is obtained (S)-1,2,3,11a-tetrahydro-6-nitro-5H-pyrrolo[2,1-c][1,4]benzodiazepine-5,11(10H)-dione with a decomposition point of 235°–237°.

(b) 57.3 g (219.3 mmol) of (S)-1,2,3,11a-tetrahydro-6-nitro-5H-pyrrolo[2,1-c][1,4]-benzodiazepine-5,11(10H)-dione are hydrogenated in 1.2 l of methanol with 3 g of 10 percent palladium/carbon at room temperature and normal pressure. After completion of the hydrogen uptake, the mixture is heated to boiling, the catalyst is filtered off under suction and the filtrate is evaporated. By recrystallization from methanol there is obtained (S)-6-amino-1,2,3,11a-tetrahydro-5H-pyrrolo[2,1-c][1,4]benzodiazepine-5,11(10H)-dione of melting point 246°–248°.

(c) A suspension of 26.8 g (115.9 mmol) of (S)-6-amino-1,2,3,11a-tetrahydro-5H-pyrrolo[2,1-c][1,4]benzodiazepine-5,11(10H)-dione in 80 ml of dry dimethylformamide is treated at −20° to −10° while stirring with 5.56 g (127.4 mmol) of sodium hydride (55 percent oil dispersion), the mixture is stirred in the above temperature range for a further 1 hour and then 19 ml (127.4 mmol) of diethylchlorophosphate are added dropwise at −45°.

Separately, 16.5 g (127.4 mmol) of potassium tert.butylate are dissolved in 23 ml of dry dimethylformamide, the solution is cooled in an acetone/dry-ice bath, treated with 18 g (127.4 mmol) of tert.butyl isocyanoacetate and the solution obtained is added dropwise at −20° to the mixture obtained according to the preceding paragraph. The resulting mixture is allowed to warm to 5°, neutralized with 7.3 ml of glacial acetic acid, poured into 500 ml of water and extracted three times with methylene chloride. The methylene chloride solution is washed once with water and once with saturated sodium chloride solution, dried over magnesium sulphate and evaporated. The crude product is crystallized from ethyl acetate/diethyl ether. By recrystallization from ethyl acetate/n-hexane there is obtained tert.butyl (S)-8-amino-11,12,13,13a-tetrahydro-9-oxo-9H-imidazo[1,5-a]pyrrolo[2,1-c][1,4]benzodiazepine-1-carboxylate with a decomposition point of 223°–224°.

(d) A mixture of 10.0 g (28.2 mmol) of tert.butyl (S)-8-amino-11,12,13,13a-tetrahydro-9-oxo-9H-imidazo[1,5-a]pyrrolo[2,1-c][1,4]benzodiazepine-1-carboxylate, 2.6 g (11.1 mmol) of a tetraethyl orthotitanate and 60 ml of cyclohexanol is stirred at 130° for 24 hours, a small amount of solvent being distilled off three times in vacuo. The mixture is subsequently evaporated in vacuo, the residue is taken up in 60 ml of chloroform, the chloroform solution is treated with water, stirred for a further 1 hour, filtered over siliceous earth and then the organic phase is separated. The organic phase is dried over magnesium sulphate and evaporated. The residue is chromatographed on silica gel while eluting with ethyl acetate and subsequently recrystallized from ethyl acetate. There is obtained cyclohexyl (S)-8-amino-11,12,13,13a-tetrahydro-9-oxo-9H-imidazo[1,5-a]pyrrolo[2,1-c][1,4]benzodiazepine-1-carboxylate of melting point 211°–212°.

EXAMPLE 51

A mixture of 3.0 g (8.2 mmol) of (S)-1-[(8-chloro-11,12,13,13a-tetrahydro-9-oxo-9H-imidazo[1,5-a]pyrrolo[2,1-c][1,4]benzodiazepin-1-yl)carbonyl]imidazole, 1.59 g (11.5 mmol) of powdered potassium carbonate, 1.43 g (11.5 mmol) of hydroquinone monomethyl ether and 20 ml of dry dimethylformamide is stirred at room temperature for 16 hours, then poured into 60 ml of water and extracted three times with methylene chloride. The organic extracts are washed twice with saturated sodium chloride solution, dried over magnesium sulphate and evaporated. After chromatography on silica gel while eluting with ethyl acetate and subsequent recrystallization from ethyl acetate there is obtained p-methoxyphenyl (S)-8-chloro-11,12,13,13a-tetrahydro-9-oxo-9H-imidazo[1,5-a]pyrrolo[2,1-c][1,4]benzodiazepine-1-carboxylate of melting point 210°–211°.

EXAMPLE 52

A mixture of 3.0 g (8.2 mmol) of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole, 1.59 g (11.5 mmol) of powdered potassium carbonate, 1.48 g (11.5 mmol) of 4-chlorophenol and 20 ml of dry dimethylformamide. is stirred at room temperature for 21 hours, then poured into 60 ml of water and extracted four times with methylene chloride. The organic extracts are washed twice with saturated sodium chloride solution, dried over magnesium sulphate and evaporated. After chromatography on silica gel while eluting with ethyl acetate and subsequent recrystallization from ethyl acetate there is obtained p-chlorophenyl (S)-8-chloro-11,12,13,13a-tetrahydro-9-oxo-9H-imidazo[1,5-a]pyrrolo[2,1-c][1,4]benzodiazepine-1-carboxylate of melting point 241°-242°.

EXAMPLE 53

A mixture of 3.0 g (8.2 mmol) of 1-[[(S)-8-chloro-11,12,13,13a-tetrahydro-9-oxo-9H-imidazo[1,5-a]pyrrolo[ 2,1-c][1,4]benzodiazepin-1-yl]carbonyl]imidazole, 1.59 g (11.5 mmol) of powdered potassium carbonate, 1.3 ml (11.5 mmol) of 2-chlorophenol and 20 ml of dry dimethylformamide is stirred at room temperature for 5 days, then poured into 60 ml of water and extracted three times with methylene chloride. The organic extracts are washed twice with saturated sodium chloride solution, dried over magnesium sulphate and evaporated. The crude product is chromatographed on silica gel, the elution being carried out successively with ethyl acetate/n-hexane (1:1), ethyl acetate/n-hexane (3:2) and ethyl acetate/n-hexane (7:3). After recrystallization from ethyl acetate, there is obtained o-chlorophenyl (S)-8-chloro-11,12,13,13a-tetrahydro-9-oxo-9H-imidazo[1,5-a]pyrrolo[2,1-c][1,4]benzodiazepine-1-carboxylate of melting point 214°-215°.

EXAMPLE 54

A mixture of 3.0 g (8.2 mmol) of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole, 1.59 g (11.5 mmol) of powdered potassium carbonate, 1.48 g (11.5 mmol) of 3-chlorophenol and 20 ml of dry dimethylformamide is stirred at room temperature for 5 days, then poured into 60 ml of water and extracted four times with methylene chloride. The organic extracts are washed once with saturated sodium chloride solution, dried over magnesium sulphate and evaporated. The residue obtained is chromatographed on silica gel while eluting with ethyl acetate and then crystallized from ethanol. There is obtained m-chlorophenyl (S)-8-chloro-11,12,13,13a-tetrahydro-9-oxo-9H-imidazo[1,5-a]pyrrolo[2,1-c][1,4]benzodiazepine-1-carboxylate of melting point 194°-195°.

EXAMPLE 55

A mixture of 3.0 g (8.2 mmol) of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole, 1.59 g (11.4 mmol) of powdered potassium carbonate, 1.48 g (11.5 mmol) of guaiacol and 20 ml of dry dimethylformamide is stirred at room temperature for 23 hours, then poured into 60 ml of water and extracted three times with methylene chloride. The organic extracts are washed twice with saturated sodium chloride solution, dried over magnesium sulphate and evaporated. The crude product is chromatographed on silica gel while eluting with ethyl acetate. After recrystallization from ethyl acetate, there is obtained o-methoxyphenyl (S)-8-chloro-11,12,13,13a-tetrahydro-9-oxo-9H-imidazo[1,5-a]pyrrolo[2,1-c][1,4]benzodiazepine-1-carboxylate of melting point 205°-206°.

EXAMPLE 56

A mixture of 3.0 g (8.2 mmol) of 1-[[(S)-8-chloro-11,12,13,13a-tetrahydro-9-oxo-9H-imidazo[1,5-a]pyrrolo[2,1-c][1,4]benzodiazepin-1-yl]carbonyl]imidazole, 1.59 g (11.5 mmol) of powdered potassium carbonate, 1.43 g (11.5 mmol) of resorcinol monomethyl ether and 20 ml of dry dimethylformamide is stirred at room temperature for 2 days, then poured into 60 ml of water and extracted three times with methylene chloride. The organic extracts are washed once with saturated sodium chloride solution, dried over magnesium sulphate and evaporated. The residue obtained is chromatographed on silica gel while eluting with ethyl acetate/n-hexane (3:1) and subsequently crystallized from ethyl acetate. There is obtained m-methoxyphenyl (S)-8-chloro-11,12,13,13a-tetrahydro-9-oxo-9H-imidazo[1,5-a]pyrrolo[2,1-c][1,4]benzodiazepine-1-carboxylate of melting point 184°-185°.

EXAMPLE 57

A mixture of 3.45 g (10 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 100 g of powdered potassium cyanide and 11.4 g (100 mmol) of cis-4-methylcyclohexanol is stirred at 130° overnight, the excess cis-4-methylhexanol is removed in vacuo and the residue is chromatographed on silica gel. By recrystallization from ethyl acetate and hexane there is obtained cis-4-methylcyclohexyl (S)-chloro-11,12,13,13a-tetrahydro-9-oxo-9H-imidazo[1,5-a]pyrrolo[2,1-c][1,4]benzodiazepine-1-carboxylate of melting point 176°-177°.

EXAMPLE 58

A mixture of 3.45 g (10 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 11.40 g (100 mmol) of cis-2-methylcyclohexanol and 0.8 g (3.5 mmol) of tetraethyl orthotitanate is stirred at 110° for 48 hours, subsequently evaporated to dryness, the residue is taken up in chloroform, the chloroform solution is stirred for 0.5 hour with 40 ml of a saturated potassium fluoride solution and the resulting emulsion is filtered through siliceous earth. The chloroform phase is separated, washed with water, dried over magnesium sulphate and concentrated. By chromatography on a silica gel column and subsequent recrystallization from ethyl acetate and hexane there is obtained cis-2-methylcyclohexyl (S)-8-chloro-11,12,13,13a-tetrahydro-9-oxo-9H-imidazo]1,5-a]pyrrolo[2,1-c][1,4]benzodiazepine-1-carboxylate as a (1:1) mixture of the two diastereoisomers of melting point 178°-180°.

EXAMPLE 59

(a) A mixture of 23.7 g (0.131 mol) of 5-fluoro-isatoic acid anhydride, 13.23 g (0.131 mol) of L-azetidine-2-carboxylic acid and 150 ml of dimethyl sulphoxide is heated to 90° for 3 hours, subsequently evaporated in a high vacuum and the residue is heated in a high vacuum for 17 hours. By recrystallization from methanol there is obtained (S)-6-fluoro-1,10a-dihydroazeto[2,1- c][1,4]benzodiazepine-4,10(2H,9H)-dione of melting point 216°-217°.

(b) A suspension of 5.5 g (125 mmol) of sodium hydride (55 percent oil dispersion) in 100 ml of dry dimethylformamide is treated at −20° to −10° while stirring with 25 g (113.5 mmol) of (S)-6-fluoro-1,10a-dihydroazeto[2,1-c][1,4]benzodiazepine-4,10(2H,9H)-dione, the mixture is stirred at the above temperature for a further 45 minutes and subsequently 18.1 ml (125 mmol) of diethylchlorophosphate are added dropwise at −40°.

Separately, 14.1 g (125 mmol) of potassium tert.butylate are dissolved in 40 ml of dry dimethylformamide, the solution is cooled in an acetone/dry-ice bath, treated with 20.9 g (125 mmol) of cyclohexyl isocyanoacetate and the solution obtained is added dropwise at −20° to −15° to the mixture obtained according to the preceding paragraph. The resulting mixture is allowed to warm to 20°, then neutralized with 7.1 ml of glacial acetic acid, poured into 600 ml of ice-water and extracted three times with methylene chloride. The organic extracts are washed successively once with water and once with saturated sodium chloride solution, dried over magnesium sulphate and evaporated. The residue is chromatographed on silica gel while eluting with ethyl acetate/n-hexane (3:2). By recrystallization from ethyl acetate there is obtained cyclohexyl (S)-7-fluoro-12,12a-dihydro-9-oxo-9H,11H-azeto[2,1-c]imidazo[1,5-a][1,4]benzodiazepine-1-carboxylate of melting point 231°-232°.

EXAMPLE 60

A mixture of 3.45 g (10 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 1 g (4.4 mmol) of tetraethyl orthotitanate and 11.4 g (100 mmol) of trans-4-methylcyclohexanol is stirred at 125° overnight, evaporated to dryness and the residue is taken up in methylene chloride. The solution is washed successively with 5N hydrochloric acid and with saturated sodium bicarbonate solution, dried over magnesium sulphate and evaporated. By recrystallization from ethyl acetate and hexane there is obtained trans-4-methylcyclohexyl (S)-8-pine-chloro- 11,12,13,13a-tetrahydro-9-oxo-9H-imidazo[1,5-a]pyrrolo[2,1-c][1,4-benzodiazepine-1-carboxylate of melting point 220°-221°.

EXAMPLE 61

A mixture of 3.0 g (7.2 mmol) of tert.butyl (S)-8-bromo-11,12,13,13a-tetrahydro-9-oxo-9H-imidazo[1,5-a]pyrrolo[2,1-c][1,4]benzodiazepine-1-carboxylate, 0.54 g (2.4 mmol) of tetraethyl orthotitanate and 6.17 g (72 mmol) of hydroxymethyl-cyclobutane is stirred at 120° for 2.5 hours, evaporated to dryness and the residue is taken up in methylene chloride. The solution is washed successively with 5N hydrochloric acid and saturated sodium bicarbonate solution, dried over magnesium sulphate and evaporated. By recrystallization from ethyl acetate there is obtained cyclobutylmethyl (S)-8-bromo-11,12,13,13a-tetrahydro-9-oxo-9H-imidazo[1,5-a]pyrrolo[2,1-c][1,4]benzodiazepine-3-carboxylate of melting point 170°-172°.

EXAMPLE 62

A mixture of 3.45 g (10 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 0.8 g (3 mmol) of tetraethyl orthotitanate and 8.61 g (100 mmol) of 1-cyclopropyl-ethanol is stirred at 115° overnight, subsequently evaporated to dryness, the residue is taken up in chloroform and chromatographed on silica gel while eluting with ethyl acetate. By recrystallization from ethyl acetate and hexane there is obtained (R,S)-1-cyclopropylethyl (S)-8-chloro-11,12,13,13a-tetrahydro-9-oxo-9H-imidazo[1,5-a]pyrrolo[2,1-c][1,4]benzodiazepine-1-carboxylate of melting point 157°-158°.

EXAMPLE 63

A mixture of 4.32 g (13.9 mmol) of ethyl (S)-11,12,13,13a-tetrahydro-9-oxo-9H-imidazo[1,5-a]pyrrolo[2,1-c][1,4]benzodiazepine-1-carboxylate, 1.52 g (6.7 mmol) of tetraethyl orthotitanate and 30 g (300 mmol) of cyclohexanol is stirred at 120° overnight, subsequently evaporated to dryness, the residue is taken up in methylene chloride, the solution is washed successively with 5N hydrochloric acid and saturated sodium bicarbonate solution, dried over magnesium sulphate and evaporated. By recrystallization from ethyl acetate there is obtained cyclohexyl (S)-11,12,13,13a-tetrahydro-9-oxo-9H-imidazo[1,5-a]pyrrolo[2,1-c][1,4-benzodiazepine-1-carboxylate of melting point 212°-213°.

EXAMPLE 64

A mixture of 3.19 g (10 mmol) of ethyl 7-chloro-5,6-dihydro-5-methyl-6-oxo-4H-imidazo[1,5-a][1,4]benzodiaze-3-carboxylate, 0.8 g (3 mmol) of tetraethyl orthotitanate and 7 g (81 mmol) of hydroxymethylcyclobutane is stirred at 125° for 5 hours, subsequently evaporated to dryness and the residue is taken up in methylene chloride. The organic solution is washed successively with 5N hydrochloric acid and with saturated sodium bicarbonate solution, dried over magnesium sulphate and evaporated. By recrystallization from ethyl acetate there is obtained cyclobutylmethyl 7-chloro-5,6-dihydro-5-methyl-6-oxo-4H-imidazo[1,5-a][1,4]benzodiazepine-3-carboxylate of melting point 181°-182°.

EXAMPLE 65

(a) A suspension of 4.43 g (101.4 mmol) of sodium hydride (55 percent oil dispersion) in 70 ml of dry dimethylformamide is treated at −20° to −30° while stirring with 20.3 g (92.2 mmol) of (S)-6-fluoro-1,10a-dihydroazeto[2,1-c][1,4]benzodiazepine-4,10(2H,9H)-dione, the mixture is stirred at the above temperature for a further 45 minutes and subsequently 15.1 ml (101.4 mmol) of diethylchlorophosphate are added dropwise at −35° to −40° C.

Separately, 11.76 g (101.4 mmol) of potassium tert.butylate are dissolved in 30 ml of dry dimethylformamide, the solution is cooled in an acetone/dry-ice bath, 14.3 g (101.4 mmol) of tert.butyl isocyanoacetate are added dropwise thereto and the solution obtained is added dropwise at −20° to −15° to the mixture obtained according to the preceding paragraph. The resulting mixture is allowed to warm to 5°, neutralized with 5.8 ml of glacial acetic acid, poured into 300 ml of water and extracted four times with methylene chloride. The organic extracts are washed twice with saturated sodium chloride solution, dried over magnesium sulphate and evaporated. The residue is chromatographed on silica gel while eluting with ethyl acetate/n-hexane (3:2). Crystallization of the oil obtained gives tert.butyl (S)-7-fluoro 12-12a-dihydro-9-oxo-9H,11H-azeto[2,1- c]imidazo[1,5-a][1,4]benzodiazepine-1-carboxylate of melting point 148°–149°.

(b) A mixture of 2.95 g (8.6 mmol) of tert.butyl (S)-7-fluoro-12,12a-dihydro-9-oxo-9H,11H-azeto[2,1-c]imidazo[1,5-a][1,4]benzodiazepine-1-carboxylate, 10 g of hydroxymethyl-cyclopropane and 1.6 g (6.8 mmol) of tetraethyl orthotitanate is stirred at 120° for 24 hours, about 3 ml of solvent being distilled off in vacuo after 1 hour. The mixture is subsequently evaporated in vacuo, the residue is dissolved in 40 ml of chloroform, the chloroform solution is treated with 30 ml of water and stirred for 1.25 hours. The mixture is filtered through siliceous earth, washed with chloroform, the chloroform phase is dried over magnesium sulphate and evaporated. The crude product is chromatographed on silica gel while eluting with ethyl acetate. After recrystallization from ethyl acetate/n-hexane, there is obtained cyclopropylmethyl (S)-7-fluoro-12,12a-dihydro-9-oxo-9H,11H-azeto[2,1-c]imidazo[1,5-a][1,4]benzodiazepine-1-carboxylate of melting point 171°–172°.

EXAMPLE 66

1.84 g (7.4 mmol) of copper sulphate pentahydrate are dissolved in 7 ml of water at 50°–60°, there are successively added dropwise a solution of 0.464 g (3.7 mmol) of anhydrous sodium sulphite in 3 ml of water and a solution of 0.54 g (11 mmol) of sodium cyanide in 2.5 ml of water and the mixture is stirred at the above temperature for a further 10 minutes. The mixture is subsequently cooled in an ice-bath, the resulting precipitate is filtered off under suction while washing with water and taken up in a solution of 0.97 g (19.8 mmol) of sodium cyanide in 6 ml of water.

Sepatately, 2.1 g (5.5 mmol) of cyclohexyl (S)-8-amino-11,12,13,13a-tetrahydro-9-oxo-9H-imidazo[1,5-a]pyrrolo[2,1-c][1,4]benzodiazepine-1-carboxylate are dissolved in a mixture of 2.8 ml of concentrated hydrochloric acid and 5.6 ml of water and a solution of 0.39 g (5.6 mmol) of sodium nitrite in 2.5 ml of water is added dropwise thereto at 0° to −3°. The resulting diazonium salt solution is added dropwise at 0° to −3° to the above copper (I) cyanide solution and the mixture is stirred without cooling for a further 1.5 hours. The mixture is subsequently made ii alkaline with 2N sodium hydroxide, treated with about 40 ml of ethyl acetate, suction filtered, the ethyl acetate phase is washed successively once with 2N sodium hydroxide solution, once with water and once with saturated sodium chloride solution, dried over magnesium sulphate and evaporated. The residue is chromatographed on silica gel while eluting with chloroform containing 0.6% methanol. After recrystallization from ethyl acetate, there is obtained cyclohexyl (S)-8-cyano-11,21,13,13a-tetrahydro-9-oxo-9H-imidazo[1,5-a]pyrrolo[2,1-c][1,4]benzodiazepine-1-carboxylate of melting point 246–247°.

EXAMPLE 67

5.29 g (27.6 mmol) of about 90 percent m-chloroperbenzoic acid are dissolved in 55 ml of methylene chloride, the solution is cooled to 0°, the suspension obtained is treated portionwise with 3.5 g (9.2 mmol) of cyclohexyl (S)-8-amino-11,12,13,13a-tetrahydro-9-oxo-9H-imidazo[1,5-a]-pyrrolo[2,1-c][1,4]benzodiazepine-1-carboxylate and the mixture is stirred without cooling for a further 2 hours. The mixture is subsequently poured into about 70 ml of ice-water, made alkaline with saturated sodium bicarbonate solution and the methylene chloride solution is separated. The methylene chloride solution is washed successively three times with saturated sodium bicarbonate solution and twice with saturated sodium chloride solution, dried over magnesium sulphate and evaporated. The residue obtained is chromatographed on silica gel while eluting with ethyl acetate. By recrystallization from ethyl acetate/n-hexane there is obtained cyclohexyl (S)-11,12,13,13a-tetrahydro-8-nitro-9-oxo-9H-imidazo[1,5-a]pyrrolo[2,1-c][1,4]benzodiazepine-1-carboxylate with a decomposition point of 204°.

EXAMPLE 68

A mixture of 6.22 g (20 mmol) of ethyl (S)-11,12,13,13a-tetrahydro-9-oxo-9H-imidazo[1,5-a]pyrrolo[2,1-c][1,4]benzodiazepine-1-carboxylate, 1.52 g (6.7 mmol) of tetraethyl orthotitanate and 10 g (194 mmol) of hydroxymethyl-cyclopropane is stirred at 115° overnight, evaporated to dryness, the residue is taken up in methylene chloride and stirred for 0.5 hour with about 50 ml of water. The emulsion obtained is filtered through siliceous earth, the organic phase is washed with saturated sodium bicarbonate solution, dried over magnesium sulphate and evaporated. By recrystallization of the residue from ethyl acetate there is obtained cyclopropylmethyl (S)-11,12,13,13a-tetrahydro-9-oxo-9H-imidazo[1,5-a]pyrrolo[2,1-c][1,4]benzodiazepine-1-carboxylate of melting point 189–190°.

EXAMPLE 69

A mixture of 9.4 g (26.1 mmol) of tert.butyl (S)-8-chloro-12,12a-dihydro-9-oxo-9H,11H-azeto[2,1-c]imidazo[1,5-a][1,4]benzodiazepine-1-carboxylate, 30 g (416 mmol) of hydroxymethyl-cyclopropane and 1.4 g (6 mmol) of tetraethyl orthotitanate is stirred at 120° for 24 hours, a small amount of solvent being distilled off in vacuo three times. The mixture is subsequently evaporated in vacuo, the residue is taken up in 60 ml of chloroform, the chloroform solution is treated with 40 ml of water and stirred for 15 hours. The mixture is then filtered through siliceous earth while washing with chloroform, the chloroform phase is dried over magnesium sulphate and evaporated. The residue is chromatographed on silica gel while eluting with ethyl acetate. After recrystallization from ethyl acetate, there is obtained cyclopropylmethyl (S)-8-chloro-12,12a-dihydro-9-oxo-9H,11H-azeto[2,1-c]imidazo[1,5-a][1,4]benzodiazepine-1-carboxylate of melting point 193–194°.

EXAMPLE 70

A mixture of 5 g (16.5 mmol) of ethyl 8-fluoro-5,6-dihydro-5-methyl-6-oxo-4H-imidazo[1,5-a][1,4]benzodiazepine-3-carboxylate, 1.8 g (8 mmol) of tetraethyl orthotitanate and 16.5 g (230 mmol) of hydroxymethyl-cyclopropane is stirred at 110° overnight, evaporated to dryness, the residue is taken up in methylene chloride and the solution obtained is stirred for 0.5 hour with 50 ml of a saturated potassium fluoride solution. The emulsion obtained is filtered through siliceous earth, the separated organic phase is washed with water, dried over magnesium sulphate and evaporated. By crystallization from ethyl acetate there is obtained cyclopropylmethyl 8-fluoro-5,6-dihydro-5-methyl-6-oxo-4H-imidazo[1,5-a][1,4]benzodiazepine-3-carboxylate of melting point 156–157°.

EXAMPLE 71

A mixture of 6.9 g (0.02 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 100 ml of allyl alcohol and 0.5 g of potassium cyanide is heated to boiling ii under reflux for 4 hours, then concentrated to half of the volume, 50 ml of allyl alcohol are added and the resulting mixture is heated to boiling under reflux for a further 10 hours. The mixture is evaporated, the residue is dissolved in chloroform, the chloroform solution is washed with water, the chloroform phase is dried over magnesium sulphate and evaporated. The residue is chromatographed on silica gel while eluting with ethyl acetate and then crystallized from ethyl acetate/hexane. There is obtained allyl (S)-8-chloro-11,12,13,13a-tetrahydro-9-oxo-9H-imidazo[1,5-a]pyrrolo[2,1-c][1,4]benzodiazepine-1-carboxylate of melting point 122°–123°.

EXAMPLE 72

(a) 11.55 g (0.05 mol) of 6-(trifluoromethyl)-isatoic acid anhydride and 5.75 g (0.05 mol) of L-proline in 100 ml of dimethyl sulphoxide are heated to 70° for 1 hour, the solvent is removed in a high vacuum and the oil obtained is heated to 170° for 15 minutes. The crude product is purified by chromatography on silica gel using methylene chloride and mixtures of methylene chloride and ethyl acetate (5%, 10%, 15%) for the elution. After recrystallization of the crude product from ethyl acetate/diethyl ether there is obtained pure (S)-1,2,3,11a-tetrahydro-6-(trifluoromethyl)-5H-pyrrolo[2,1-c][1,4]benzodiazepine-5,11(10H)-dione of melting point 176–178°.

(b) A solution of 9.15 g (32.2 mmol) of (S)-1,2,3,11a-tetrahydro-6-(trifluoromethyl)-5H-pyrrolo[2,1-c][1,4]benzodiazepine-5,11(10H)-dione in 30 ml of dry dimethylformamide is treated at −20° to 10° while stirring with 1.54 g (35.4 mmol) of sodium hydride (55 percent oil dispersion), the mixture is stirred in the above temperature range for a further 1 hour and then 5.3 ml (35.4 mmol) of diethylchlorophosphate are added dropwise at −40°.

Separately, 3.97 g (35.4 mmol) of potassium tert.butylate are dissolved in 9 ml of dry dimethylformamide, the solution is cooled in an acetone/dry-ice bath and treated with 4.99 g (35.4 mmol) of tert.butyl isocyanoacetate. The solution obtained is added dropwise at −20° to the mixture obtained according to the preceding paragraph. The resulting mixture is allowed to warm to 10°, neutralized with 2.0 ml of glacial acetic acid, poured into 150 ml of water and extracted three times with methylene chloride. The methylene chloride solution is washed once with water, dried over magnesium sulphate, evaporated and the crude product obtained is chromatographed on silica gel while eluting with ethyl acetate. Subsequent crystallization from diethyl ether yields tert.butyl (S)-11,12,13,13a-tetrahydro-9-oxo-8-(trifluoromethyl)-9H-imidazo[1,5-a]pyrrolo[2,1-c][1,4]benzodiazepine-1-carboxylate of melting point 201°–203°.

(c) A mixture of 2.88 g (7.1 mmol) of tert.butyl (S)-11,12, 3,13a-tetrahydro-9-oxo-8-(trifluoromethyl)-9H-imidazo[1,5-a]pyrrolo[2,1-c][1,4-benzodiazepine-1-carboxylate, 1.0 g (4.2 mmol) of tetraethyl orthotitanate and 15 g of cyclohexanol is stirred at 120° for 22 hours, about 3 ml of solvent being distilled off in vacuo four times. The mixture is subsequently evaporated in vacuo, the residue is taken up in 40 ml of chloroform, the chloroform solution is treated with 25 ml of water and stirred for 1.25 hours. The mixture is subsequently suction filtered through siliceous earth, the organic phase is separated, the aqueous phase is extracted once with chloroform, the combined chloroform extracts are dried over magnesium sulphate and evaporated. By crystallization of the residual oil from ethyl acetate/n-hexane there is obtained cyclohexyl (S)-11,12,13,13a-tetrahydro-9-oxo-8-(trifluoromethyl)-9H-imidazo[1,5-a]pyrrolo[2,1-c][1,4]benzodiazepine-1-carboxylate of melting point 193°–194°.

EXAMPLE 73

(a) 4-Chloro-5-fluoro-isatin is obtained from 3-chloro-4-fluoro-aniline according to the Sandmeyer isatin synthesis [T. Sandmeyer, Helv. 2, 234 (1919)]. Separation of the isomers according to P. W. Sadler, J. Org. Chemistry 21, 169 (1956) yields, after recrystallization, pure 4-chloro-5-fluoro-isatin of melting point 249°–251°.

(b) 7.8 g (0.039 mol) of 4-chloro-5-fluoro-isatin are suspended in 50 ml of 100 percent acetic acid, treated with 0.25 ml of concentrated sulphuric acid and then 4.4 ml (0.043 mol) of 30 percent hydrogen peroxide are added dropwise thereto. The mixture is subsequently heated to 70° for 2.5 hours, then cooled to 10° and filtered. The crude product is recrystallized from acetone/hexane, there being obtained 6-chloro-5-fluoro-isatoic acid anhydride of melting point 275°–278° (decomposition).

(c) 3.3 g (0.015 mol) of 6-chloro-5-fluoro-isatoic acid anhydride and 2 g (0.017 mol) of L-proline in 7.5 ml of dimethylformamide are heated to 120° for 2 hours, cooled, treated with 12 ml of distilled water and the separated brown crystals are filtered off. By recrystallization of the crude product from acetone/hexane there is obtained (S)6-chloro-7-fluoro-1,2,3,11a-tetrahydro-5H-pyrrolo[2,1-c][1,4]benzodiazepine-5,11(10H)-dione of melting point 217°–219°.

(d) A solution of 7.16 g (26.6 mmol) of (S)-6-chloro-7-fluoro-1,2,3,11a-tetrahydro-5H-pyrrolo[2,1-c][1,4]benzodiazepine-5,11(10H)-dione in 25 ml of dry dimethylformamide is treated at −20° to −10° while stirring with 1.27 g (29.26 mmol) of sodium hydride (55 percent oil dispersion), the mixture is stirred in the above temperature range for a further 1.25 hours and then 4.4 ml (29.26 mmol) of diethylchlorophosphate are added dropwise at −40°.

Separately, 3.28 g (29.3 mmol) of potassium tert.butylate are dissolved in 8 ml of dry dimethylformamide, the solution is cooled in an acetone/dry-ice bath, treated with 4.13 g (29.3 mmol) of tert.butyl isocyanoacetate and the solution obtained is added dropwise at −20° to −10° to the mixture obtained according to the preceding paragraph. The resulting solution is allowed to warm to 10°, neutralized with 1.7 ml of glacial acetic acid, poured into 150 ml of water and extracted three times with methylene chloride. The methylene chloride solution is washed once with water, dried over magnesium sulphate, evaporated and the crude product obtained is chromatographed on silica gel while eluting with ethyl acetate. By crystallization from diethyl ether there is obtained tert.butyl (S)-8-chloro-7-fluoro-11,12,13,13a-tetrahydro-9-oxo-9H-imidazo[1,5-a]pyrrolo[2,1-c][1,4]benzodiazepine-1-carboxylate of melting point 211°–212°.

(e) A mixture of 4.0 g (10 mmol) of tert.butyl (S)-8-chloro-7-fluoro-11,12,13,13a-tetrahydro-9-oxo-9H-imidazo[1,5-a]pyrrolo[2,1-c][1,4]benzodiazepine-1-carboxylate, 0.8 g (3 mmol) of tetraethyl orthotitanate and 15 ml of cyclohexanol is stirred at 120° overnight, evaporated to dryness, the residue is taken up in methylene chloride, the solution obtained is washed successively with 40 ml of 5N hydrochloric acid, water and saturated sodium bicarbonate solution, dried over magnesium sulphate and evaporated. There is obtained cyclohexyl (S)-8-chloro-7-fluoro-11,12,13,13a-tetrahydro-9-oxo-9H-imidazo[1,5-a]pyrrolo[2,1-c][1,4]benzodiazepine-1-carboxylate of melting point 163°–166°.

EXAMPLE 74

A mixture of 3.6 g (10 mmol) of tert.butyl (S)-8-chloro-12,12a-dihydro-9-oxo-9H,11H-azeto[2,1-c]imidazo[1,5-a][1,4]benzodiazepine-1-carboxylate, 1.7 g (7.2 mmol) of tetraethyl orthotitanate and 20 ml of 3-methoxybenzyl alcohol is stirred at 120° for 5 hours, a small amount of solvent being removed in vacuo three times during this time. The excess 3-methoxybenzyl alcohol is subsequently distilled off in a high vacuum, the residue is taken up in 30 ml of chloroform, the chloroform solution is treated with 25 ml of water, stirred for 1.25 hours and filtered through siliceous earth. The organic phase is separated, the aqueous phase is extracted once with chloroform, the combined chloroform extracts are dried over magnesium sulphate and evaporated. The crude product is chromatographed on silica gel while eluting with ethyl acetate. By recrystallization from ethyl acetate/n-hexane there is obtained m-methoxybenzyl (S)-8-chloro-12,12a-dihydro-9-oxo-9H,11H-azeto[2,1-c]imidazo[1,5-a][1,4]benzodiazepine-1-carboxylate of melting point 126°–127°.

EXAMPLE 75

A mixture of 3.45 g (10 mmol) of ethyl (S)-8-chloro-11,12,13,13a-tetrahydro-9-oxo-9H-imidazo[1,5-a]pyrrolo[2,1-c][1,4]benzodiazepine-1-carboxylate, 0.17 g (0.72 mmol) of tetraethyl orthotitanate and 7.5 g of 2-cyclopropyl-ethanol is stirred at 130° for 14.5 hours, about 2 ml of solvent being distilled off after 0.5 hour. The mixture is subsequently evaporated to dryness in vacuo, the residue is taken up in chloroform and chromatographed on silica gel while eluting with ethyl acetate. After crystallization of the resulting oil from ethyl acetate/n-hexane, there is obtained 2-cyclopropylethyl (S)-8-chloro-11,12,13,13a-tetrahydro-9-oxo-9H-imidazo[1,5-a]pyrrolo[2,1-c][1,4]benzodiazepine-1-carboxylate of melting point 163°–164°.

EXAMPLE 76

A mixture of 1.58 g (4.4 mmol) of cyclopropyl (S)-8-chloro-12,12a-dihydro-9-oxo-9H,11H-azeto[2,1-c]imidazo[1,5-a][1,4]benzodiazepine-1-carboxylate, 1.3 g (5.5 mmol) of tetraethyl orthotitanate and 15 g of 1-cyclopropyl-ethanol is stirred at 120° for 16 hours. The mixture is then evaporated to dryness in vacuo, the residue is taken up in methylene chloride and chromatographed on silica gel while eluting with ethyl acetate. By recrystallization from ethyl acetate/n-hexane there is obtained (R,S)-1-cyclopropylethyl (S)-8-chloro-12,12a-dihydro-9-oxo-9H,11H-azeto[2,1-c]imidazo[1,5-a][1,4]benzodizepine-1-carboxylate of melting point 187°–188° (mixture of the two diastereoisomers).

Cyclohexyl (S)-8-bromo-11,12,13,13a-tetrahydro-9-oxo-9H-imidazo[1,5-a]pyrrolo[2,1-c][1,4]benzodiazepine-1-carboxylate can be used as the active substance for the manufacture of the pharmaceutical preparations described in Examples A to C hereinafter:

EXAMPLE A

Tablets containing the following ingredients are manufactured in the usual manner:

|  | mg/tablet |
|---|---|
| Active substance | 5 |
| Lactose | 45 |
| Maize starch | 15 |
| Microcrystalline cellulose | 34 |
| Magnesium stearate | 1 |
| Tablet weight | 100 |

EXAMPLE B

Capsules containing the following ingredients are manufactured:

|  | mg/capsule |
|---|---|
| Active substance | 10 |
| Lactose | 155 |
| Maize starch | 30 |
| Talc | 5 |
| Capsule fill weight | 200 |

The active substance, lactose and maize starch are firstly mixed in a mixer and then in a comminuting machine. The mixture is returned to the mixer, the talc is added thereto and the resulting mixture is mixed thoroughly. The mixture is then filled by machine into hard gelatine capsules.

EXAMPLE C

Suppositories containing the following ingredients are manufactured:

|  | mg/suppository |
|---|---|
| Active substance | 15 |
| Suppository mass | 1285 |
| Total | 1300 |

The suppository mass is melted in a glass or steel vessel, mixed thoroughly and cooled to 45°. There is then added thereto the finely powdered active substance and the mixture is stirred until it is completely dispersed. The mixture is poured into suppository moulds of suitable size and left to cool. The suppositories are then removed from the moulds and packed individually in wax paper or metal foil.

The compounds of formula I listed hereinafter can be used as the active substance in Examples A, B and C in place of cyclohexyl (S)-8-bromo-11,12,13,13a-tetrahydro-9-oxo-9H-imidazo[1,5-a]pyrrolo[2,1-c][1,4]benzodiazepine-1-carboxylate:

Cyclopropylmethyl (S)-8-chloro-12,12a-dihydro-9-oxo-9H,11H-azeto[2,1-c]imidazo[1,5-a][1,4-benzodiazepine-1-carboxylate, cyclohexyl (S)-8-chloro-7-fluoro-11,12,13,13a-tetrahydro-9-oxo-9H-imidazo[1,5-a]pyrrolo[2,1-c][1,4]benzodiazepine-1-carboxylate, cyclopropylmethyl (S)-7-fluoro-11,12,13,13a-tetrahydro-9-oxo-9H-imidazo[1,5-a]pyrrolo[2,1-c][1,4]benzodiazepine-1-carboxylate, cyclohexyl (S)-8-bromo-11,12,13,13a-tetrahydro-9-oxo-9H-imidazo[1,5-a]pyrrolo[2,1-c][1,4]benzodiazepine-1-carboxylate, (R,S)-1-cyclopropylethyl (S)-8-chloro-11,12,13,13a-tetrahydro-9-oxo-9H-imidazo[1,5-a]pyrrolo[2,1-c][1,4]benzodiazepine-1-carboxylate,
cyclohexyl (S)-7-fluoro-12,12a-dihydro-9-oxo-9H,11H-azeto[2,1-c]imidazo[1,5-a][1,4]benzodiazepine-1-carboxylate,
(R,S)-2-cyclohexen-1-yl (S)-8-chloro-11,12,13,13a-tetrahydro-9-oxo-9H-imidazo[1,5-a]pyrrolo[2,1-c][1,4]benzodiazepine-1-carboxylate,
(R,S)-1-cyclopropylethyl (S)-8-chloro-12,12a-dihydro-9-oxo-9H,11H-azeto[2,1-c]imidazo[1,5-a][1,4]benzodizepine-1-carboxylate,
cyclohexyl (S)-12,12a-dihydro-8-iodo-9-oxo-9H,11H-azeto[2,1-c]imidazo[1,5-a][1,4]benzodiazepine-1-carboxylate,
cyclopropylmethyl (S)-7-fluoro-12,12-dihydro-9-oxo-9H-imidazo[1,5-a]pyrrolo[2,1-c][1,4]benzodiazepine-1-carboxylate,
cyclohexyl (S)-11,12,13,13a-tetrahydro-9-oxo-8-(trifluoromethyl)-9H-imidazo[1,5-a]pyrrolo[2,1-c][1,4]benzodiazepine-1-carboxylate and
cyclohexyl (S)-8-chloro-12,12a-dihydro-9-oxo-9H,11H-azeto[2,1-c]imidazo[1,5-a][1,4]benzodiazepine-1-carboxylate.

What is claimed is:

1. A compound of the formula

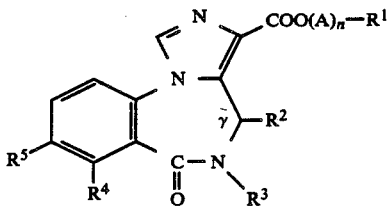

I wherein A is lower alkylene, n is zero or 1, R¹ is selected from the group consisting of lower alkynyl, lower alkenyl, phenyl optionally substituted by halogen, lower alkyloxy, lower alkyl, trifluoromethyl or nitro, (C₃₋₈)-cycloalkyl optionally substituted by lower alkyl or (C₅₋₈)-cycloalkenyl optionally substituted by lower alkyl, or a 5- or 6-membered saturated or unsaturated heterocycle which contains either one oxygen or one sulphur atom as a ring member and which is optionally substituted by lower alkyl, R⁴ and R⁵ each are hydrogen, halogen, trifluoromethyl, cyano, nitro, amino or lower alkyl and either R² is hydrogen and R³ is lower alkyl or R² is hydrogen and R³ is lower alkyl or R² and R³ together are dimethylene, trimethylene or propenylene, the compounds of formula I in which R² and R³ together are dimethylene, trimethylene or propenylene having the (S) or (R,S) configuration with reference to the carbon atom denoted by γ,
and pharmaceutically acceptable acid addition salts thereof.

2. The compound of claim 1, wherein n is zero or n is 1 and A is methylene or 1,2-ethylene optionally substituted by lower alkyl.

3. The compound of claim 2, wherein R¹ is lower alkynyl, phenyl, (C₃₋₈)-cycloalkyl optionally substituted by lower alkyl or (C₅₋₈)-cycloalkenyl optionally substituted by lower alkyl.

4. The compound of claim 3, wherein R¹ is (C₃₋₆)-cycloalkyl optionally substituted by lower alkyl.

5. The compound of claim 1, wherein the group —(A)ₙ—R¹ is cyclohexyl, 2-cyclohexen-1-yl, cyclopropylmethyl, 1-cyclopropylethyl or 2-cyclopropylethyl.

6. The compound of claim 5, wherein R² and R³ together are dimethylene, trimethylene or propylene and the corresponding compounds having the (S) configuration with reference to the carbon atom denoted by γ.

7. The compound of claim 6, wherein R⁴ is hydrogen, halogen, trifluoromethyl, nitro, cyano or lower alkyl.

8. The compound of claim 7, wherein R⁵ is hydrogen or halogen.

9. A compound of claim 1: cyclopropylmethyl(S)-8-chloro-12,12a-dihydro-9-oxo-9H,11H-azeto[2,1-c]imidazo[1,5-a][1,4]benzodiazepine-1-carboxylate.

10. A compound of claim 1: cycohexyl(S)-8-bromo-11,12,13,13a-tetrahydro-9-oxo-9H-imidazo[1,5-a]pyrrolo[2,1-c][1,4]benzodiazepine-1-carboxylate.

11. A compound of claim 1: (R,S)-2cyclohexen-1-yl(S)8-chloro-11,12,13,13a-tetrahydro-9-oxo-9H-imidazo[1,5-a]pyrrolo[2,1-c][1,4]benzodiazepine-1-carboxylate.

12. A compound of claim 1: cycohexyl (S)-8-chloro-12,12a-dihydro-9-oxo-9H,11H-azeto[2,1-c]imidazo[1,5-a][1,4]benzodiazepine-1-carboxylate.

13. A compound of claim 1: cyclohexyl(S)-7-fluoro-12,12a-dihydro-9-oxo-9H,11H-azeto[2,1-c]imidazo[1,5-a][1,4]benzodiazepine-1-carboxylate.

14. A compound of claim 1: cyclohexyl(S)-8-chloro-7-fluro-11,12,13,13a-tetrahydro-9-oxo-9H-imidazo[1,5-a]pyrrolo[2,1-c][1,4]benzodiazepine-1-carboxylate.

15. A compound of claim 1: (R,S)-1-cyclopropylethyl (S)-8-chloro-12,12a-dihydro-9-oxo-9H,11H-azeto[2,1-c]imidazo[1,5-a][1,4]benzodiazepine-1-carboxylate.

16. A compound of claim 1: cyclohexyl (S)-12,12a-dihydro-8-iodo-9-oxo-9H,11H-azeto[2,1-c]imidazo[1,5-a][1,4]benzodiazepine-1-carboxylate.

17. A compound of claim 1: cyclopropyl methyl (S)-7-fluoro-11,12,13,13a-tetrahydro-9-oxo-9H-imidazo[1,5-a]pyrrolo[2,1-c][1,4]benzodiazepine-1-carboxylate.

18. A compound of claim 1: (R,S)-1-Cyclopropylethyl(S)-8-chloro-11,12,13,13a-tetrahydro-9-oxo-9H-imidazo[1,5-a]pyrrolo[2,1-c][1,4]benzodiazepine-1-carboxylate.

19. A compound of claim 1: cyclopropylmethyl(S)-7-fluro-12,12a-dihydro-9-oxo-9H,11H-azeto[2,1-c]imidazo[1,5-a][1,4]benzodiazepine-1-carboxylate.

20. A compound of claim 1: cyclohexyl(S)-11,12,13,13a-tetrahydro-9-oxo-8-(trifluoromethyl)-9H-imidazo[1,5-a]pyrrolo[2,1-c][1,4]benzodiazepine-1-carboxylate.

21. A compound of claim 1 selected from the group consisting of cyclohexyl (S)-8-chloro-11,12,13,13a--tetrahydro-9-oxo-9H-imidazo[1,5-a]pyrrolo[2,1-c][1,4-]benzodiazepine-1-carboxylate,2-propynyl(S)-8-chloro-11,12,13,13a-tetrahydro-9-oxo-9H-imidazo[1,5-a]pyrrolo[2,1-c][1,4]benzodiazepine-1-carboxylate, cyclopropylmethyl 8-chloro-11,13a-dihydro-9-oxo-9H-imidazo[1,5-a]pyrrolo[2,1-c][1,4]benzodiazepine-1-carboxylate, cyclopropylmethyl (S)-8-chloro-11,12,13,13a-tetrahydro-9-oxo-9H-imidazo[1,5-a]pyrrolo[2,1-c][1,4]benzodiazepine-1-carboxylate, cyclopropylmethyl (S)-8-bromo-11,12,13,13a-tetrahydro-9-oxo-9H-imidazo[1,5-a]pyrrolo[2,1-c][1,4]benzodiazepine-1-carboxylate, cyclopropylmethyl (S)-11,12,13,13a-tetrahydro-8-iodo-9-oxo-9H-imidazo[1,5-a]pyrrolo[2,1-c][1,4]benzodiazepine-1-carboxylate, 2-cyclopropylethyl (S)-8-chloro-11,12,13,13a-tetrahydro-9-oxo-9H-imidazo[1,5-a]pyrrolo[2,1-c][1,4]benzodiazepine-1-carboxylate, cyclohexyl (S)-12,12a-dihydro-8-methyl-9-oxo-9H,11H-azeto[2,1-c]imidazo[1,5-a][1,4]benzodiazepine-1-carboxylate, rac-cis-3-methylcyclohexyl (S)-8-chloro-11,12,13,13a-tetrahydro-9-oxo-9H-imidazo[1,5-a]pyrrolo[2,1-c][1,4]benzodiazepine-1-carboxylate, cyclopentyl (S)-12,12a-dihydro-8-iodo-9-oxo-9H,11H-azeto[2,1-c]imidazo[1,5-a][1,4]benzodiazepine-1-carboxylate, cycloheptyl (S)-8-chloro-11,12,13,13a-tetrahydro-9-oxo-9H-imidazo[1,5-a]pyrrolo[2,1-c][1,4]benzodiazepine-1-carboxylate, benzyl (S)-8-chloro-12,12a-dihydro-9-oxo-9H,11H-azeto[2,1-c]imidazo[1,5-a][1,4]benzodiazepine-1-carboxylate, cyclopropylmethyl (S)-12,12a-dihydro-8-iodo-9-oxo-9H,11H-azeto[2,1-c]imidazo[1,5-a][1,4]benzodiazepine-1-carboxylate, cyclohexyl (S)-8-bromo-12,12a-dihydro-9-oxo-9H,11H-azeto[2,1-c]imidazo[1,5-a][1,4]benzodiazepine-1-carboxylate, cyclopropylmethyl (S)-8-bromo-12,12a-dihydro-9-oxo-9H,11H-azeto[2,1-c]imidazo[1,5-a][1,4]benzodiazepine-1-carboxylate, cyclohexyl (S)-11,12,13,13a-tetrahydro-8-nitro-9-oxo-9H-imidazo[1,5-a]pyrrolo[2,1-c][1,4]benzodiazepine-1-carboxylate and cyclohexyl(S)-8-cyano-11,12,13, 13a-tetrahydro-9-oxo-9H-imidazo-[1,5-a]pyrrolo[2,1-c][1,4]benzodiazepine-1-carboxylate.

22. A process to produce a compound of the formula

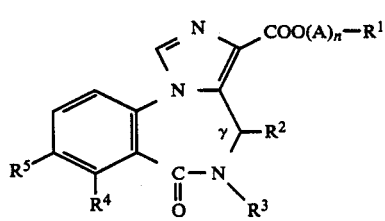   I wherein A is lower alkylene, n is zero or 1, $R^1$ is selected from the group consisting of lower alkynyl, lower alkenyl, aryl, $(C_{3-8})$-cycloalkyl optionally substituted by lower alkyl or $(C_{5-8})$-cycloalkenyl optionally substituted by lower alkyl or a 5- or 6-membered saturated or unsaturated heterocycle which contains an oxygen or sulphur atom as a ring member and which is optionally substituted by lower alkyl, $R^4$ and $R^5$ each are hydrogen, halogen, trifluoromethyl, cyano, nitro, amino or lower alkyl and either $R^2$ is hydrogen and $R^3$ is lower alkyl or $R^2$ and $R^3$ together are dimethylene, trimethylene or propenylene, the compounds of formula I in which $R^2$ and $R^3$ together are dimethylene, trimethylene or propenylene having the (S) or (R,S) configuration with reference to the carbon atom denoted by $\gamma$, and pharmaceutically acceptable acid addition salts thereof, which comprises (a) trans-esterifying a carboxylic acid ester of the formular

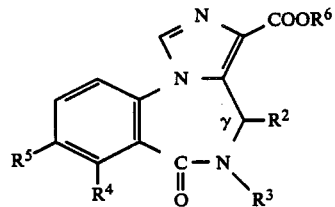   II wherein $R^6$ is lower alkyl or the group $—(A)_n—R^1$ and A, n, $R^1$, $R^2$, $R^3$, $R^4$, and $R^5$ are as above with an alcohol of the formula HO—(A)$_n$—R$^1$   III wherein A, n and $R^1$ are as above
which yields the desired group $—(A)_n—R^1$, or
(b) esterifying a carboxylic acid of the formula

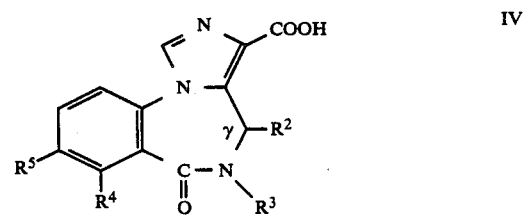   IV wherein $R^2$, $R^3$, $R^4$ and $R^5$ are as above
with an agent which yields the group $—(A)_n—R^12$,
$R^3$, $R^4$ and $R^5$ are as above
with an agent which yields the group $—(A)_n—R^1$, or
(c) reacting a compound of the formula

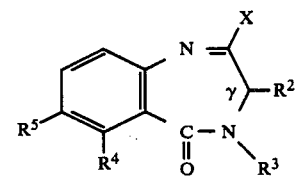   V wherein X is a leaving group and $R^2$, $R^3$, $R^4$ and $R^5$ are as above,
in the presence of a base with an isocyanoacetic ester of the formula CN—CH$_2$—COO—(A)$_n$—R$^1$   VI wherein A, n and $R^1$ are as above or
(d) replacing the halogen atom in a compound of formula I in which one of $R^4$ and $R^5$ is halogen and the other is hydrogen, trifluoromethyl, amino, nitro, cyano or lower alkyl and A, n, $R^1$, $R^2$ and $R^3$ are as above by the cyano group, or
(e) replacing the amino group in a compound of formula I in which one of $R^4$ and $R^5$ is amino and the other is hydrogen, halogen, trifluoromethyl, nitro, cyano or lower alkyl and A, n, $R^1$, $R^2$ and $R^3$ are as above by a hydrogen or halogen atom or by a cyano or nitro group, or
(f) halogenating a compound of formula I in which one of $R^4$ and $R^5$ is amino and the other is hydrogen and A, n, $R^1$, $R^2$ and $R^3$ are as above in the a-position to the amino group, or
(g) reducing the nitro group in a compound of formula I in which one of $R^4$ and $R^5$ is nitro and the other hydrogen and A, n, $R^1$, $R^2$ and $R^3$ are as above to the amino group, and
(h) if desired, converting a compound of formula I obtained into a pharmaceutically acceptable acid additon salt.

* * * * *